(12) United States Patent
Mino

(10) Patent No.: US 11,974,806 B2
(45) Date of Patent: May 7, 2024

(54) OPHTHALMOLOGIC INFORMATION PROCESSING APPARATUS, OPHTHALMOLOGIC APPARATUS, OPHTHALMOLOGIC INFORMATION PROCESSING METHOD, AND RECORDING MEDIUM

(71) Applicant: TOPCON CORPORATION, Tokyo (JP)

(72) Inventor: Toshihiro Mino, West New York, NJ (US)

(73) Assignee: TOPCON CORPORATION, Tokyo (JP)

( * ) Notice: Subject to any disclaimer, the term of this patent is extended or adjusted under 35 U.S.C. 154(b) by 660 days.

(21) Appl. No.: 17/179,416

(22) Filed: Feb. 19, 2021

(65) Prior Publication Data
US 2022/0265136 A1 Aug. 25, 2022

(51) Int. Cl.
*A61B 3/00* (2006.01)
*A61B 3/10* (2006.01)
(Continued)

(52) U.S. Cl.
CPC ............ *A61B 3/0025* (2013.01); *A61B 3/102* (2013.01); *G06T 5/70* (2024.01); *G06T 7/55* (2017.01);
(Continued)

(58) Field of Classification Search
CPC ....... A61B 3/0025; A61B 3/102; G06T 5/002; G06T 7/55; G06T 2207/10101; G06T 2207/30041
See application file for complete search history.

(56) References Cited

U.S. PATENT DOCUMENTS

2014/0221827 A1\* 8/2014 Motaghiannezam ........................ A61B 5/1128
356/479
2015/0009507 A1\* 1/2015 Yasuno .................. A61B 3/102
356/479
(Continued)

FOREIGN PATENT DOCUMENTS

JP 2019-154985 A 9/2019

OTHER PUBLICATIONS

Shemonski et al., "Three-Dimensional Motion Correction Using Speckle and Phase for in vivo Computed Optical Interferometric Tomography", Biomedical Optics Express, vol. 5, No. 12, Dec. 1, 2014, pp. 4131-4143.
(Continued)

*Primary Examiner* — Nay A Maung
*Assistant Examiner* — Jose M Torres
(74) *Attorney, Agent, or Firm* — XSENSUS LLP

(57) ABSTRACT

An ophthalmologic information processing apparatus according to the embodiments include a generator, an extractor, and a phase correction unit. The generator is configured to generate a phase difference profile by performing averaging processing in a depth direction on phase differences obtained by calculating for each depth position of A-lines between two adjacent B-frames of complex OCT data of a subject's eye. The extractor is configured to a phase drift from the phase difference profile generated by the generator. The phase correction unit is configured to correct a phase of first complex OCT data of any one of the two B-frames based on the phase drift extracted by the extractor.

16 Claims, 21 Drawing Sheets

(51) Int. Cl.
*G06T 5/70* (2024.01)
*G06T 7/55* (2017.01)

(52) U.S. Cl.
CPC ............... *G06T 2207/10101* (2013.01); *G06T 2207/30041* (2013.01)

(56) References Cited

U.S. PATENT DOCUMENTS

| | | | | |
|---|---|---|---|---|
| 2015/0168127 A1* | 6/2015 | Takeno | ................ | A61B 5/7203 |
| | | | | 356/479 |
| 2016/0320171 A1* | 11/2016 | Hanebuchi | ......... | G01B 9/02087 |
| 2019/0282083 A1 | 9/2019 | Hayashi et al. | | |
| 2020/0284572 A1* | 9/2020 | Ford | .................. | G01B 9/02083 |

OTHER PUBLICATIONS

Oikawa et al., "Bulk Phase Error Correction for Holographic Signal Processing of Optical Coherence Tomography", Proceedings of SPIE, vol. 11521, 2020, pp. 115210P-1-15210P-3.

* cited by examiner

OPHTHALMOLOGIC INFORMATION PROCESSING APPARATUS, OPHTHALMOLOGIC APPARATUS, OPHTHALMOLOGIC INFORMATION PROCESSING METHOD, AND RECORDING MEDIUM

FIELD

The disclosure relates to an ophthalmologic information processing apparatus, an ophthalmologic apparatus, an ophthalmologic information processing method, and a recording medium.

BACKGROUND

CAO (Computational Adaptive Optics) is a technique for correcting aberrations caused by an object to be measured or an optical system using arithmetic processing. CAO can improve the measurement accuracy by correcting the measurement data based on the aberration information acquired using known hardware such as a wavefront sensor.

For example, "Three-dimensional motion correction using speckle and phase for in vivo computed optical interferometric tomography" (Nathan D. Shemonski et al., BIOMEDICAL OPTICS EXPRESS, 4 Nov. 2014, Vol. 5, No. 12, pp. 4131-4143), and "Bulk phase error correction for holographic signal processing of optical coherence tomography" (Kensuke Oikawa et al, Proc.SPIE11521, Biomedical Imaging and Sensing Conference 2020, 115210P (15 Jun. 2020); doi: 10.1117/12. 2573231) disclose methods in which such CAO are applied to optical coherence tomography (OCT) systems.

SUMMARY

One aspect of some embodiments is an ophthalmologic information processing apparatus, including: a generator configured to generate a phase difference profile by performing averaging processing in a depth direction on phase differences obtained by calculating for each depth position of A-lines between two adjacent B-frames of complex OCT data of a subject's eye; an extractor configured to a phase drift from the phase difference profile generated by the generator; and a phase correction unit configured to correct a phase of first complex OCT data of either one of the two B-frames based on the phase drift extracted by the extractor.

Another aspect of some embodiments is a ophthalmologic apparatus, including: a measurement system configured to acquire the complex OCT data by performing optical coherence tomography on the subject's eye; and the ophthalmologic information processing apparatus described above.

Still another aspect of some embodiments is an ophthalmologic information processing method, including: a generation step of generating a phase difference profile by performing averaging processing in a depth direction on phase differences obtained by calculating for each depth position of A-lines between two adjacent B-frames of complex OCT data of a subject's eye; an extraction step of extracting a phase drift from the phase difference profile generated in the generation step; and a phase correction step of correcting a phase of first complex OCT data of either one of the two B-frames based on the phase drift extracted in the extraction step.

Still another aspect of some embodiments is a computer readable non-transitory recording medium in which a program for causing a computer to execute each step of the ophthalmologic information processing method described above is recorded.

It should be noted that the configurations according to a plurality of aspects described above can be combined arbitrarily.

DETAILED DESCRIPTION

Figure 1:
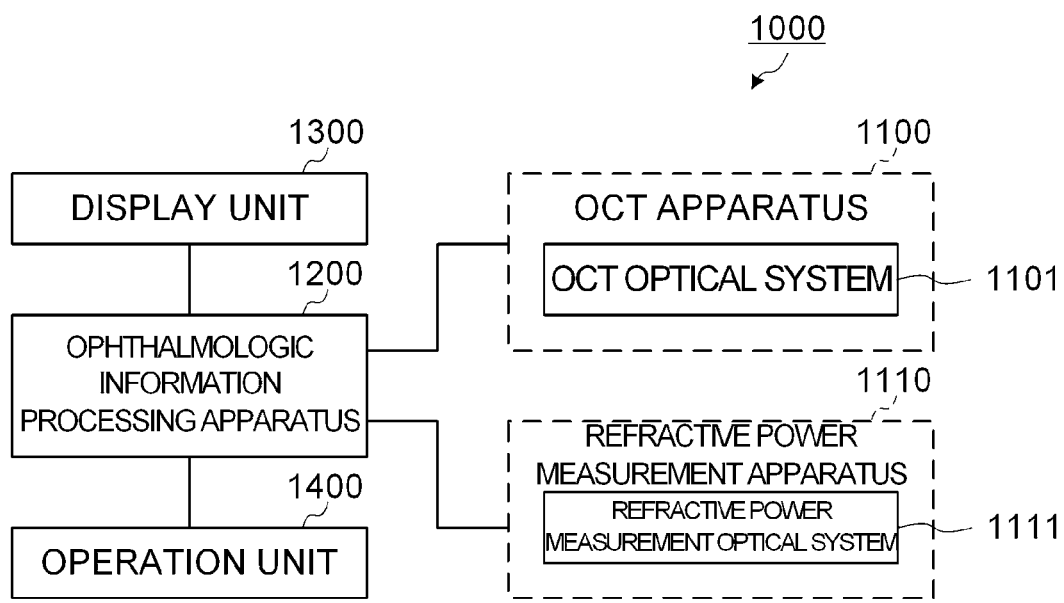
FIG. 1 is a schematic diagram illustrating an example of the configuration of an ophthalmologic system according to embodiments.

Phase information included in the measurement data acquired by performing OCT is useful in applications such as OCT angiography (OCTA) and CAO-OCT in which CAO is applied to OCT. This phase information is affected by a phase drift caused by the movement of the object to be observed and phase instability in the measurement system. Therefore, by stabilizing the phase so as not to be affected by the phase drift, the accuracy of OCTA and CAO-OCT can be improved.

For example, the phase can be stabilized by calculating the phase difference between the measurement data of adjacent positions and canceling the calculated phase difference. This is based on the premise that it can be assumed that the expected value of the phase difference becomes zero for an object to be measured consisting of innumerable scatterers such as a retina of the subject's eye. However, in reality, there is a deviation/error from this assumption, and as the phase correction is repeated by the above method, the phase error is integrated, and the influence of the integrated error may not be negligible.

According to some embodiments of the present invention, a new technique for stabilizing the phase included in the measurement data acquired by performing OCT can be provided.

Referring now to the drawings, exemplary embodiments of an ophthalmologic information processing apparatus, an ophthalmologic apparatus, an ophthalmologic information processing method, a program, and a recording medium according to the present invention are described below. Any of the contents of the documents cited in the present specification and arbitrary known techniques may be applied to the embodiments below.

An ophthalmologic information processing apparatus according to embodiments acquires OCT data (measurement data, complex OCT data) from an ophthalmologic apparatus (OCT apparatus) provided outside the ophthalmologic information processing apparatus. The ophthalmologic apparatus provided outside the ophthalmologic information processing apparatus acquires the complex OCT data by performing OCT on the subject's eye. The ophthalmologic information processing apparatus can perform phase stabilization processing on the complex OCT data of the subject's eye. Specifically, the ophthalmologic information processing apparatus generates a phase difference profile obtained by averaging phase differences in a depth direction, the phase differences being obtained by calculating for each depth position of A-lines between two adjacent B-frames of the complex OCT data, and extracts a phase drift from the generated phase difference profile. The ophthalmologic information processing apparatus corrects a phase of the complex OCT data based on the extracted phase drift. At this time, the ophthalmologic information processing apparatus can remove less reliable phase difference data from the phase difference profile, and can extract the phase drift from the phase difference profile from which the less reliable phase difference data has been removed. This allows to obtain the OCT data on which the phase stabilization processing has is performed, without being affected by noise or structure-derived phase shift. As a result, OCT data robust to phase changes and phase noise caused by the movement of a subject's eye and phase instability in the OCT measurement system can be obtained.

For example, the ophthalmologic information processing apparatus can correct an aberration caused by the subject's eye or an optical system with respect to the OCT data in which the phase has been corrected described above. Specifically, the ophthalmologic information processing apparatus searches for an optimal CAO filter (parameter(s) of the CAO filter) for correcting the aberration, and performs aberration correction processing on the OCT data using the searched CAO filter. For example, in the case where the ophthalmologic information processing apparatus is configured to be capable of acquiring refractive power information representing the refractive power of the subject's eye from the ophthalmologic apparatus (refractive power measurement apparatus) provided outside the ophthalmologic information processing apparatus, the ophthalmologic information processing apparatus can calculate parameter(s) (filter information) of the CAO filter based on the acquired refractive power information. The ophthalmologic information processing apparatus can display, on a display means, aberration information (specifically, aberration information on a pupil surface of the subject's eye) corresponding to the searched CAO filter (parameter(s)).

The ophthalmologic apparatus according to the embodiments has the function of the ophthalmologic information processing apparatus according to the embodiments, in addition to the function of at least one of OCT measurement function and refractive power measurement function.

An ophthalmologic information processing method according to the embodiments includes one or more steps for realizing the processing executed by a processor (computer) in the ophthalmologic information processing apparatus according to the embodiments. A program according to the embodiments causes the processor to execute each step of the ophthalmologic information processing method according to the embodiments. A recording medium according to the embodiments is a computer readable non-transitory recording medium (storage medium) on which the program according to the embodiments is recorded.

The term "processor" as used herein refers to a circuit such as, for example, a central processing unit (CPU), a graphics processing unit (GPO, an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Hereinafter, in the embodiments, the case of using the swept source type OCT method in the measurement (or the photographing) using OCT will be described. However, the configuration according to the embodiments can also be applied to in the measurement using an ophthalmologic apparatus perform other type of OCT (for example, spectral domain type OCT).

In this specification, an image acquired using OCT may be collectively referred to as an "OCT image". Also, the measurement operation for forming OCT images may be referred to as OCT measurement.

The ophthalmologic apparatus according to some embodiments includes any one or more of an ophthalmologic imaging apparatus, an ophthalmologic measuring apparatus, and an ophthalmologic therapy apparatus. The ophthalmologic imaging apparatus included in the ophthalmologic apparatus according to some embodiments includes, for example, any one or more of a fundus camera, a scanning laser ophthalmoscope, a slit lamp ophthalmoscope, a surgical microscope, and the like. Further, the ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. Further, the ophthalmologic therapy apparatus included in the ophthalmologic apparatus according to some embodiments includes any one or more of a laser therapy apparatus, a surgical apparatus, a surgical microscope, and the like, for example.

<Ophthalmologic System>

An ophthalmologic system according to the embodiments includes a function of the ophthalmologic information processing apparatus according to the embodiments and a function of the ophthalmologic apparatus according to the embodiments.

FIG. 1 shows a block diagram of a first configuration example of the ophthalmologic system according to the embodiments.

An ophthalmologic system 1000 according to the first configuration example of the embodiments includes an OCT apparatus 1100 as the ophthalmologic apparatus, a refractive power measurement apparatus 1110 as the ophthalmologic apparatus, the ophthalmologic information processing apparatus 1200, a display unit 1300, and an operation unit 1400. The ophthalmologic information processing apparatus 1200 may include the function of at least one of the display unit 1300 and the operation unit 1400.

The ophthalmologic information processing apparatus 1200 and the OCT apparatus 1100 are connected so as to be capable of communicating via a wired or wireless communication path. Further, the ophthalmologic information processing apparatus 1200 and the refractive power measurement apparatus 1110 are connected so as to be capable of communicating via a wired or wireless communication path.

The OCT apparatus 1100 includes an OCT optical system 1101 for performing OCT (OCT measurement) on the subject's eye. The OCT apparatus 1100 sends complex OCT data acquired by performing OCT to the ophthalmologic information processing apparatus 1200. For example, the OCT optical system 1101 may have a known configuration as disclosed in Japanese Unexamined Patent Application Publication No. 2019-154985.

The refractive power measurement apparatus 1110 includes a refractive power measurement optical system 1111 for measuring the refractive power of the subject's eye. The refractive power measurement apparatus 1110 sends the refractive power information representing the refractive power of the subject's eye by measuring refractive power to the ophthalmologic information processing apparatus 1200. For example, the refractive power measurement optical system 1111 may have a known configuration as disclosed in Japanese Unexamined Patent Application Publication No. 2019-154985.

The ophthalmologic information processing apparatus 1200 generates the phase difference profile obtained by averaging the phase differences in the depth direction, the phase differences being obtained by calculating for each depth position of A-lines between two adjacent B-frames of complex OCT data of a subject's eye from the OCT apparatus 1100. The ophthalmologic information processing apparatus 1200 extracts the phase drift from the generated phase difference profile, and corrects the phase of the complex OCT data of one of the above two adjacent B-frames based on the extracted phase drift.

Further, the ophthalmologic information processing apparatus 1200 searches for an optimal CAO filter (parameter(s) of the CAO filter) for correcting the aberration in the complex OCT data in which the phase has been corrected. The ophthalmologic information processing apparatus 1200 performs aberration correction processing on the complex OCT data using the searched CAO filter. The ophthalmologic information processing apparatus 1200 can simplify or omit the search processing of the CAO filter described above, by calculating the parameter(s) of the CAO filter using the refractive power information (measurement result of the refractive power) of the subject's eye from the refractive power measurement apparatus 1110.

The ophthalmologic information processing apparatus 1200 can display an OCT image formed based on the complex OCT data or an aberration information on a pupil surface of the subject's eye, on the display unit 1300. Here, the complex OCT data has been performed aberration correction processing using the searched CAO filter, and the aberration information corresponds to the searched CAO filter.

The ophthalmologic information processing apparatus 1200 can control the display unit 1300 or the processing executed inside the apparatus, based on an operation information corresponds to an operation content of the user from the operation unit 1400. For example, the ophthalmologic information processing apparatus 1200 changes (modifies) the parameter(s) of the CAO filter based on the operation information from the operation unit 1400, and performs the aberration correction processing on the complex OCT data using the CAO filter whose parameter(s) has (have) been changed. The ophthalmologic information processing apparatus 1200 forms the OCT image based on the complex OCT data in which the aberration has been corrected. For example, the ophthalmologic information processing apparatus 1200 changes the parameter(s) of the CAO filter based on the operation information from the operation unit 1400, and displays, on the display unit 1300, the aberration information on the pupil surface of the subject's eye corresponding to the CAO filter whose parameter(s) has (have) been changed.

In the ophthalmologic system 1000 shown in FIG. 1, the ophthalmologic information processing apparatus 1200 may be configured to obtain the OCT data and the refractive power information from the ophthalmologic apparatus having the function of the OCT measurement and the function of refractive power measurement.

In some embodiments, the ophthalmologic apparatus includes the function of the ophthalmologic information processing apparatus according to the embodiments.

Figure 2:
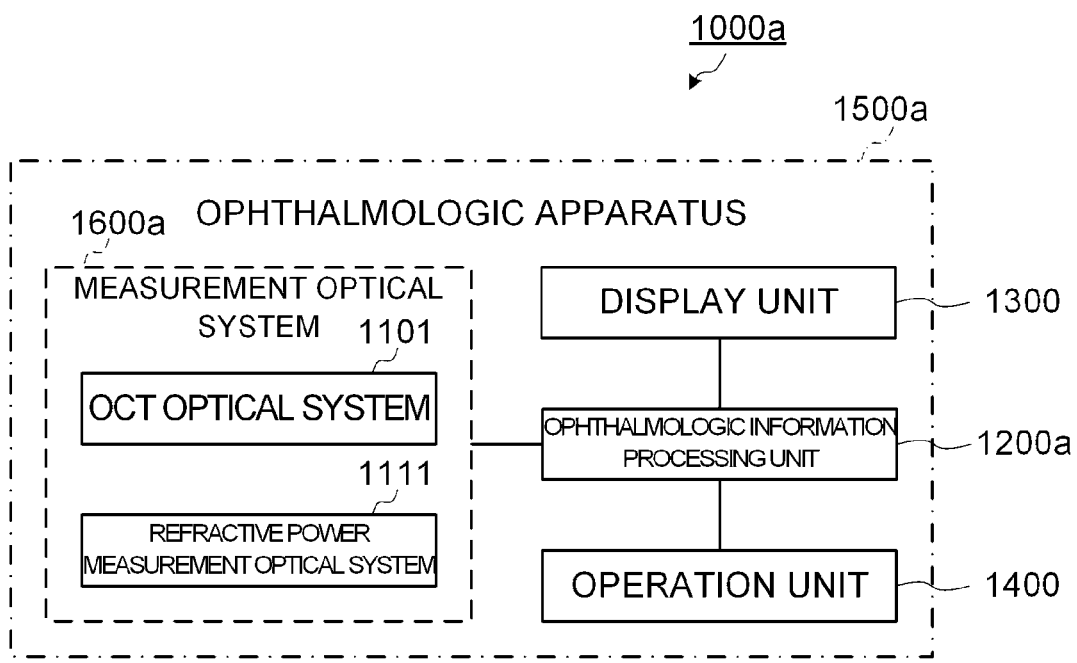
FIG. 2 is a schematic diagram illustrating an example of the configuration of an ophthalmologic system according to embodiments.

FIG. 2 shows a block diagram of a second configuration example of the ophthalmologic system according to the embodiments. In FIG. 2, like reference numerals designate like parts as in FIG. 1. The same description may not be repeated.

An ophthalmologic system 1000a according to the second configuration example of the embodiments includes an ophthalmologic apparatus 1500a that realizes the functions of the ophthalmologic system 1000 according to the first configuration example by itself. The ophthalmologic apparatus 1500a includes an ophthalmologic information processing unit 1200a, the display unit 1300, the operation unit 1400, and a measurement optical system 1600a. The measurement optical system 1600a includes the OCT optical system 1101 and the refractive power measurement optical system 1111. The ophthalmologic information processing unit 1200a has the function of the ophthalmologic information processing apparatus 1200 shown in FIG. 1, and controls each part of the ophthalmologic apparatus 1500a.

In FIG. 2, the ophthalmologic apparatus having the function the OCT measurement and the function of the ophthalmologic information processing apparatus according to the embodiments may be configured to obtain the refractive power information from the ophthalmologic apparatus having the function of refractive power measurement.

Figure 3:
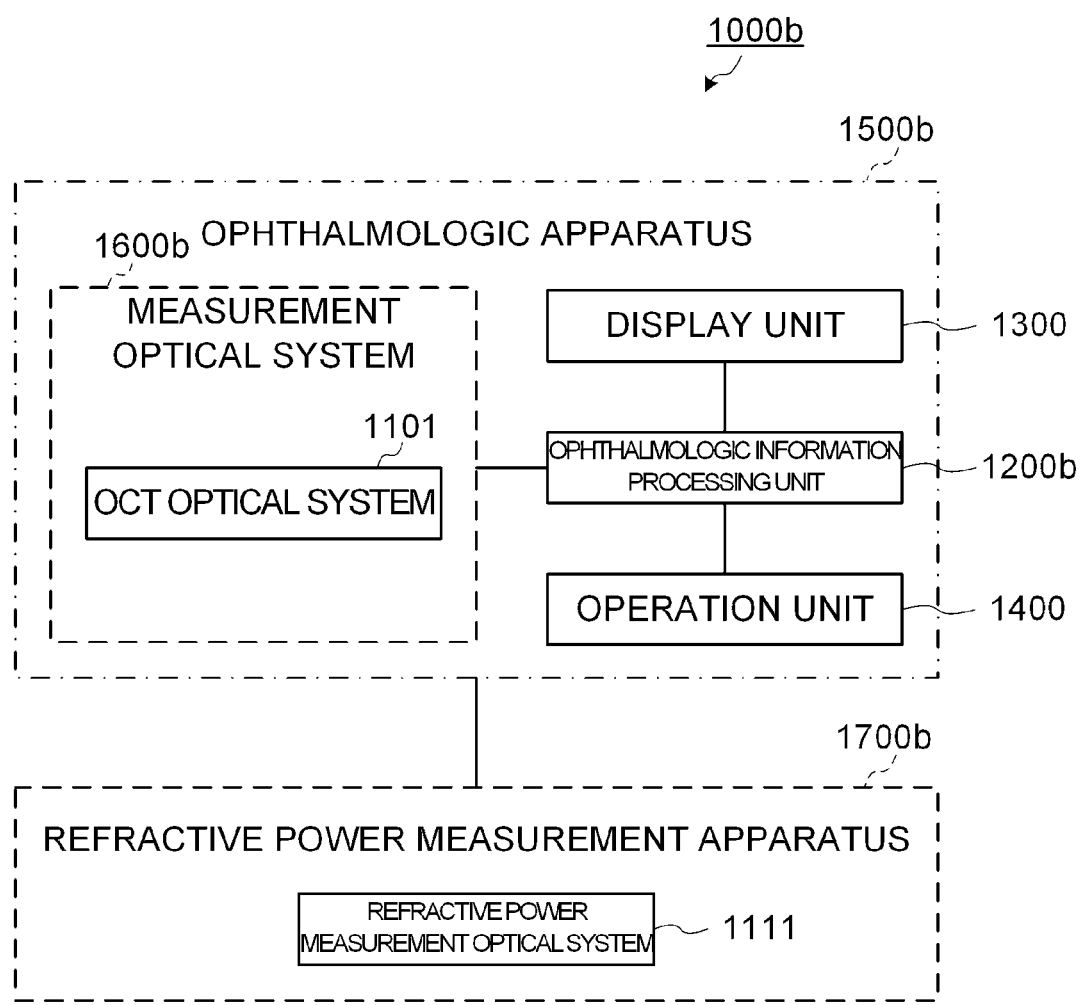
FIG. 3 is a schematic diagram illustrating an example of the configuration of an ophthalmologic system according to embodiments.

FIG. 3 shows a block diagram of a third configuration example of the ophthalmologic system according to the embodiments. In FIG. 3, like reference numerals designate like parts as in FIG. 1 or FIG. 2. The same description may not be repeated.

An ophthalmologic system 1000b according to the third configuration example of the embodiments includes an ophthalmologic apparatus 1500b and a refractive power measurement apparatus 1700b. The ophthalmologic apparatus 1500b and the refractive power measurement apparatus 1700b are connected so as to be capable of communicating via a wired or wireless communication path.

The ophthalmologic apparatus 1500b includes an ophthalmologic information processing unit 1200b, the display unit 1300, the operation unit 1400, and a measurement optical system 1600b. The measurement optical system 1600b includes the OCT optical system 1101. The ophthalmologic information processing unit 1200b controls each part of the ophthalmologic apparatus 1500b.

The refractive power measurement apparatus 1700b includes the refractive power measurement optical system 1111. The refractive power measurement apparatus 1700b sends the refractive power representing the refractive power of the subject's eye by measuring refractive power to the ophthalmologic apparatus 1500b.

In FIG. 3, the ophthalmologic apparatus having the function of the refractive power measurement and the function of the ophthalmologic information processing apparatus according to the embodiments may be configured to obtain the OCT data from the ophthalmologic apparatus having the function of the OCT measurement.

Hereinafter, the configuration and the operation of the embodiments will be described with reference to the ophthalmologic apparatus according to the third configuration example.

The ophthalmologic apparatus according to the following embodiments includes an OCT apparatus and a fundus camera. The OCT apparatus can perform OCT measurement. However, the configuration according to the following embodiments may be applied to a single-functional OCT apparatus.

Further, hereinafter, an ophthalmologic apparatus capable of performing OCT measurement on a fundus of the subject's eye will be mainly described as an example. However, the ophthalmologic apparatus according to the embodiments may be capable of performing OCT measurement on an anterior segment of the subject's eye. In some embodiments, a measurement site of the OCT measurement and/or a range of the OCT measurement are changed by moving a lens for changing focal position of the measurement light. In some embodiments, the ophthalmologic apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmologic apparatus for measuring fundus, OCT measurement is performed on the anterior segment, by making the measurement light incident on the subject's eye, the measurement light having been converted into a parallel light flux by arranging a front lens between the objective lens and the subject's eye.

<Ophthalmologic Apparatus>
[Configuration]
(Optical System)

Figure 4:
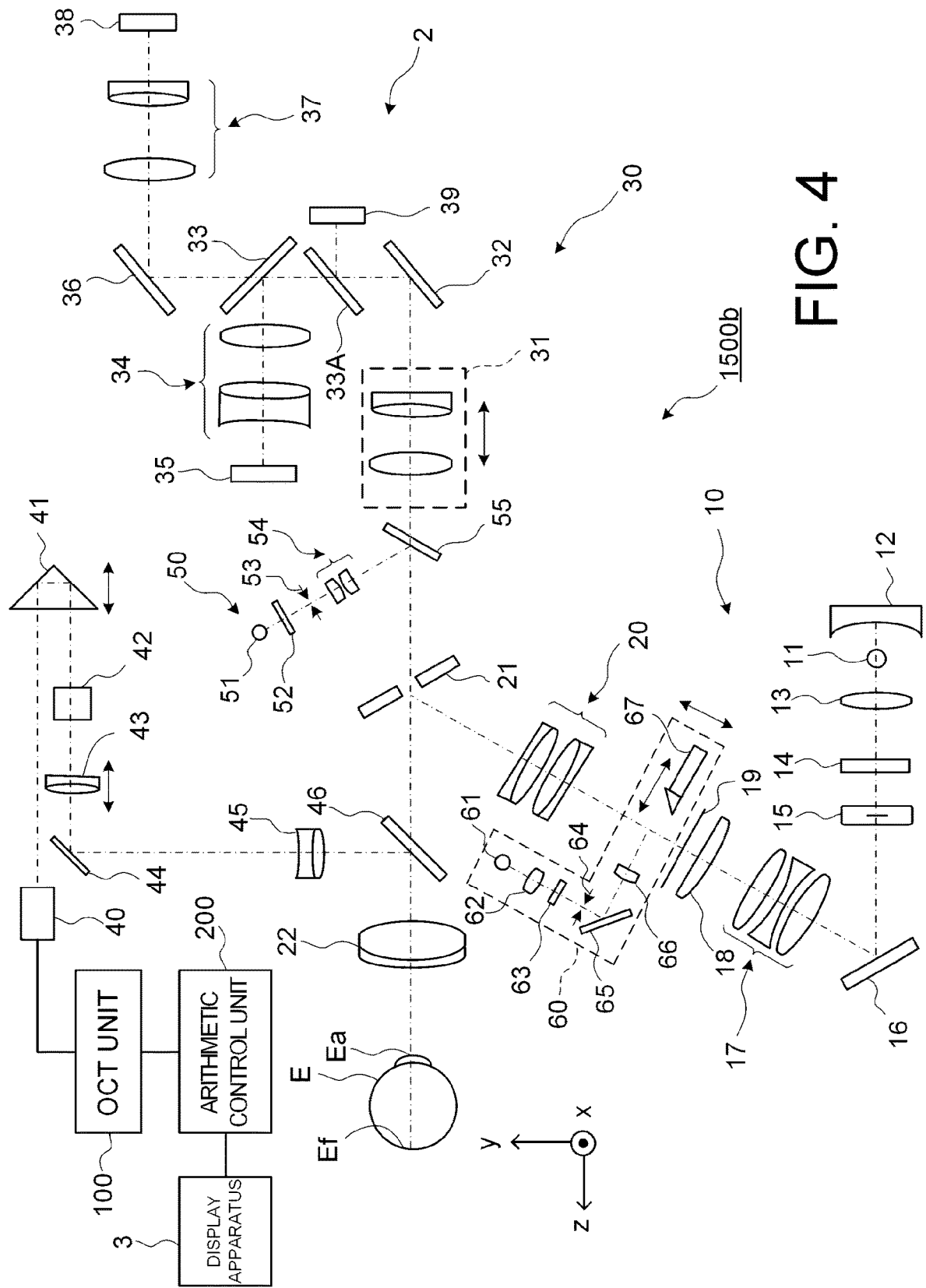
FIG. 4 is a schematic diagram illustrating an example of the configuration of an optical system of an ophthalmologic apparatus according to the embodiments.

FIG. 4 illustrates an example of the configuration of an optical system of the ophthalmologic apparatus 1500b according to the embodiments. Hereinafter, a direction of an optical axis of an objective lens 22 (the traveling direction of measurement light LS described later) is defined as a z direction, a horizontal direction orthogonal to the z direction is defined as an x direction, and a vertical direction orthogonal to the z direction is defined as a y direction.

The ophthalmologic apparatus 1500b includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1500b. In some embodiments, the lens unit is configured to be manually inserted and removed between the subject's eye E and an objective lens 22 described later. In some embodiments, the lens unit is configured to be automatically inserted and removed between the subject's eye E and an objective lens 22 described later, under the control of the arithmetic control unit 200 (control unit 210 described later).

(Fundus Camera Unit 2)

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a photographic image, or the like. The observation image is obtained by moving image shooting using near infrared light. The photographic image is a still image using flash light. Furthermore, the fundus camera unit 2 can obtain the front image (anterior segment image) by photographing (imaging) an anterior segment Ea of the subject's eye E.

The fundus camera unit 2 includes an illumination optical system 10 and an imaging (photographing) optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after being transmitted through a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, is transmitted through a dichroic mirror 46, and is refracted by an objective lens 22, thereby illuminating the subject's eye E (fundus Ef or anterior segment Ea). Returning light of the observation illumination light reflected from the subject's eye E is refracted by the objective lens 22, is transmitted through the dichroic mirror 46, passes through the hole part formed in the center region of the perforated mirror 21, is transmitted through a dichroic mirror 55. The returning light transmitted through the dichroic mirror 55 travels through a photography focusing lens 31 and is reflected by a mirror 32. Further, this returning light is transmitted through a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) emitted from the imaging light source 15 is projected onto the fundus Ef via the same route as that of the observation illumination light. Returning light of the imaging illumination light from the subject's eye E is guided to the dichroic mirror 33 via the same route as that of the observation illumination light, is transmitted through the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light output from the LCD 39 is reflected by the half mirror 33A, is reflected by the mirror 32, travels through the photography focusing lens 31 and the dichroic mirror 55, and passes through the hole part of the perforated mirror 21. The light flux (beam) having passed through the hole part of the perforated mirror 21 is transmitted through the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmologic apparatus 1500b according to some embodiments includes GUI (Graphical User Interface) and the like for designating at least one of such fixation positions. The ophthalmologic apparatus 1500b according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmologic apparatus 1500b may be provided with one or more external fixation light sources. One of the one or more external fixation light sources can project fixation light onto a fellow eye of the subject's eye E. A projected position of the fixation light on the fellow eye can be changed. By changing the projected position of the fixation light on the fellow eye, the fixation position of the subject's eye E can be changed. The fixation position projected by the external fixation light source(s) may be the same as the fixation position of the subject's eye E using the LCD 39. For example, the movable fixation target can be generated by selectively turning on the plurality of external fixation light sources. Alternatively, the movable fixation target can be generated using one or more movable external fixation light sources.

The alignment optical system 50 generates an alignment indicator for alignment of the optical system with respect to the subject's eye E. Alignment light emitted from an LED 51 travels through the diaphragms 52 and 53 and the relay lens 54, is reflected by the dichroic mirror 55, and passes through the hole part of the perforated mirror 21. The alignment light having passed through the hole part of the perforated mirror 21 is transmitted through the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To conduct focus adjustment, the reflective surface of the reflection rod 67 is arranged in a slanted position on the illumination optical path. Focus light emitted from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, is transmitted through the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof.

The dichroic mirror 46 combines an optical path for fundus photography and an optical path for OCT. The dichroic mirror 46 reflects light of wavelength band used in OCT, and transmits light for fundus photography. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is movable in directions indicated by the arrow in FIG. 4, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate with the pupil of the subject's eye E. The optical scanner 42 deflects the measurement light LS traveling along the OCT optical path. The optical scanner 42 can deflect the measurement light LS in a one-dimensionally or two-dimensional manner.

In case that the optical scanner deflects the measurement light LS in a one-dimensionally manner, the optical scanner 42 includes a galvano scanner capable of deflecting the measurement light LS within a predetermined deflection angle range in a predetermined deflection direction. In case that the optical scanner deflects the measurement light LS in a two-dimensionally manner, the optical scanner 42 includes a first galvano scanner and a second galvano scanner. The first galvano scanner deflects the measurement light LS so as to scan a photographing (imaging) site (fundus Ef or the anterior segment) in a horizontal direction orthogonal to the optical axis of the OCT optical system 8. Here, the OCT optical system 8 is an optical system in the path from the interference optical system included in the OCT unit 100, which will be described later, to the objective lens 22. The second galvano scanner deflects the measurement light LS deflected by the first galvano mirror so as to scan the photographing site in a vertical direction orthogonal to the optical axis of the OCT optical system 8. Examples of scan mode with the measurement light LS performed by the optical scanner 42 include a horizontal scan, a vertical scan, a cross scan, a radial scan, a circle scan, a concentric scan, a helical (spiral) scan, and the like.

The OCT focusing lens 43 is moved along the optical path of the measurement light LS in order to perform focus adjustment of the optical system for OCT. The OCT focusing lens 43 can move within a moving range. The moving range includes a first lens position for placing the focal position of the measurement light LS at the fundus Ef or near the fundus Ef of the subject's eye E and a second lens position for making the measurement light LS projected onto the subject's eye E a parallel light beam. The movement of the photography focusing lens 31, the movement of the focus optical system 60, and the movement of the OCT focusing lens 43 can be controlled in conjunction with each other.

(OCT Unit 100)

Figure 5:
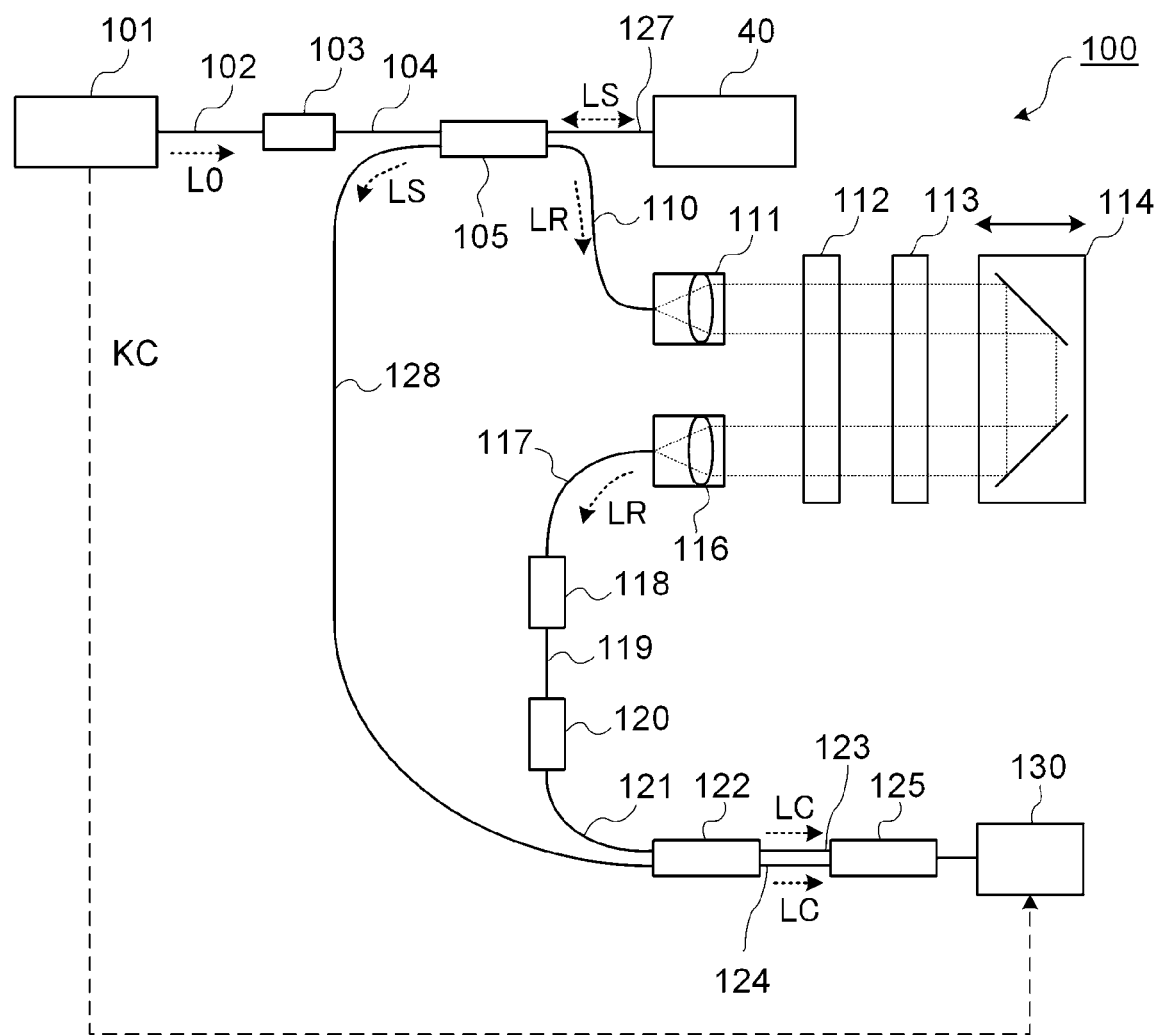
FIG. 5 is a schematic diagram illustrating an example of the configuration of an optical system of an ophthalmologic apparatus according to the embodiments.

An example of the configuration of the OCT unit 100 is shown in FIG. 5. The OCT unit 100 is provided with an optical system for performing OCT measurement (or OCT photographing) on the subject's eye E. The optical system includes an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic control unit 200.

Like swept source type ophthalmologic apparatuses commonly used, the light source unit 101 includes a wavelength sweeping type (i.e., a wavelength scanning type) light source capable of sweeping (scanning) the wavelengths of emitted light. The wavelength sweeping type light source includes a laser light source that includes a resonator. The light source unit 101 temporally changes the output wavelengths within the near-infrared wavelength bands that cannot be visually recognized with human eyes.

Light L0 output from the light source unit 101 is guided to the polarization controller 103 through the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose the polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The optical path length changing unit 114 is movable in directions indicated by the arrow in FIG. 5, thereby changing the length of the optical path of the reference light LR. Through such movement, the length of the optical path of the reference light LR is changed. The change in the optical path length is used for the correction of the optical path length according to the axial length of the subject's eye E, for the adjustment of the interference state, or the like. The optical path length changing unit 114 includes, for example, a corner cube and a movement mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

The configuration shown in FIG. 4 and FIG. 5 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

Meanwhile, the measurement light LS generated by the fiber coupler 105 is guided through the optical fiber 127, and is made into the parallel light beam by the collimator lens unit 40. The measurement light LS made into the parallel light flux is guided to the dichroic mirror 46 via the optical path length changing unit 41, the optical scanner 42, the OCT focusing lens 43, the mirror 44, and the relay lens 45. The measurement light LS guided to the dichroic mirror 46 is reflected by the dichroic mirror 46, refracted by the objective lens 22, and projected onto the subject's eye E. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength sweeping type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs sampling of the detection result obtained by the detector 125 based on the clock KC. The DAQ 130 sends the result of the sampling of the detection result obtained by the detector 125 to the arithmetic control unit 200. For example, the arithmetic control unit 200 performs the Fourier transform etc. on the spectral distribution based on the detection result obtained by the detector 125 for each series of wavelength scanning (i.e., for each A-line). With this, a complex amplitude profile or a reflection intensity profile is formed for each A-line. In addition, the arithmetic control unit 200 forms image data by applying imaging processing to the complex amplitude profile or the reflection intensity profiles for the respective A-lines.

(Processing System)

The processing system (control system) of the ophthalmologic apparatus 1500b is configured with the arithmetic control unit 200 as a center.

(Arithmetic Control Unit 200)

The arithmetic control unit 200 forms an OCT image of the fundus Ef from the detection signal fed from the DAQ 130. The arithmetic processing therefor is performed in the same manner as in the conventional swept-source-type OCT apparatus.

The arithmetic control unit 200 controls each part of the fundus camera unit 2, the display apparatus 3, and the OCT unit 100. Hereinafter, the function of the display apparatus 3 shall be realized by a user interface including a display unit and an operation unit.

Figure 6:
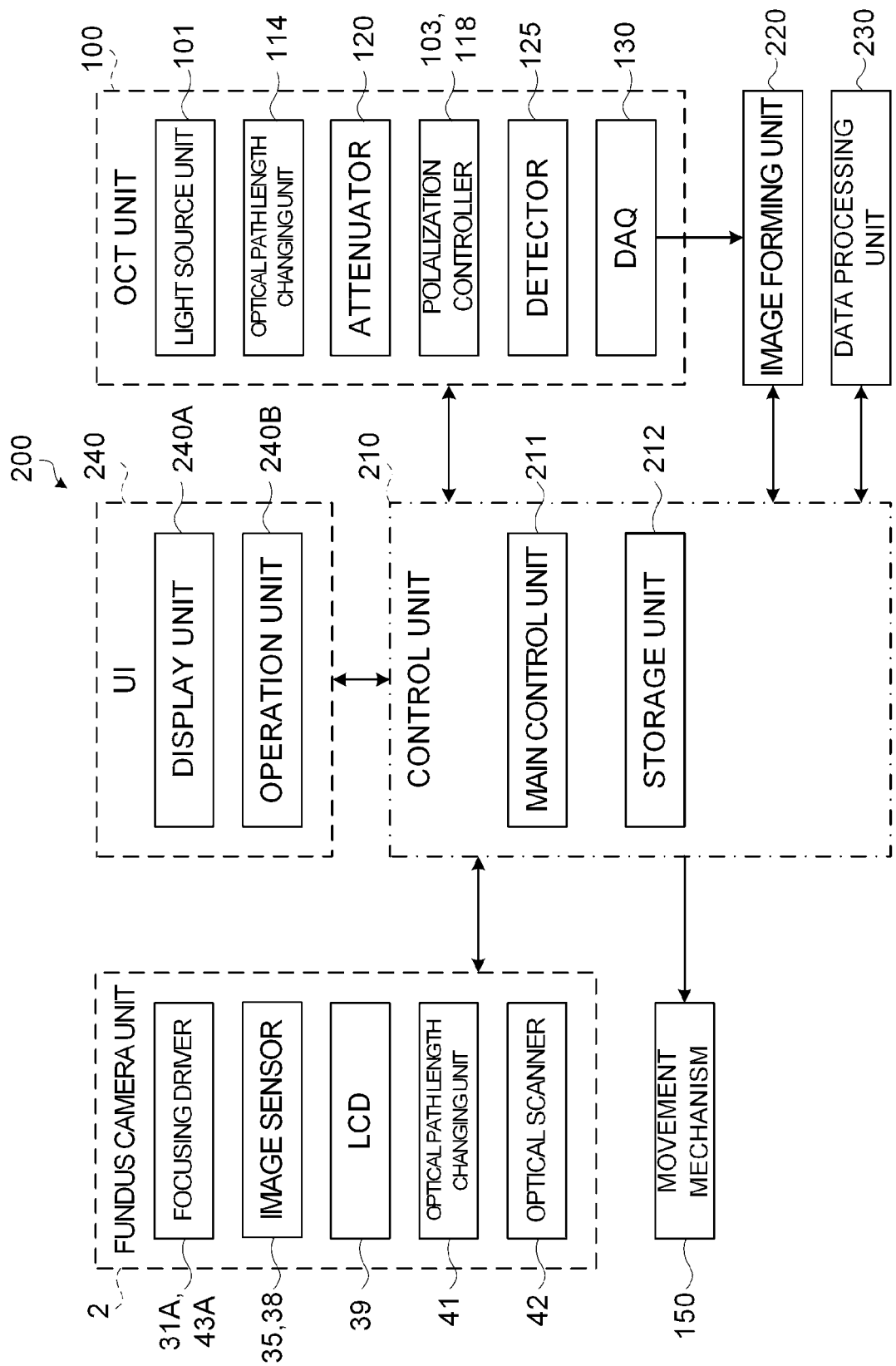
FIG. 6 is a schematic diagram illustrating an example of the configuration of a processing system of the ophthalmologic apparatus according to the embodiments.

FIG. 6 is a functional block diagram illustrating an example of the configuration of the processing system of the ophthalmologic apparatus 1500b. In FIG. 6, a part of the components included in the ophthalmologic apparatus 1500b is omitted.

The arithmetic control unit 200 includes the control unit 210, an image forming unit 220, and a data processing unit 230. The functions of the arithmetic control unit 200 are realized by one or more processors. In some embodiments, the function of the arithmetic control unit 200 is realized by a control processor that realizes the function of the control unit 210, an image forming processor that realizes the function of the image forming unit 220, and a data processing processor that realizes the function of the data processing unit 230.

(Control Unit 210)

The control unit 210 executes various controls. The control unit 210 includes a main control unit 211 and a storage unit 212.

(Main Control Unit 211)

The main control unit 211 includes a processor and controls each part of the ophthalmologic apparatus 1500b.

As the control of the fundus camera unit 2, the main control unit 211 performs following controls: the operation controls of the observation light source 11, the imaging light source 15, the CCD image sensors 35, 38; the operation controls of the LEDs 51 and 61; the operation control of the LCD 39; the movement control of the photography focusing lens 31; the movement control of the OCT focusing lens 43; the movement control of the reflection rod 67; the control of the alignment optical system 50; the movement control of the focus optical system 60; the movement control of the optical path length changing unit 41; the operation control of the optical scanner 42, and the like.

As the control of the OCT unit 100, the main control unit 211 performs following controls: the operation control of the light source unit 101; the movement control of the optical path length changing unit 114; the operation control of the attenuator 120; the operation control of the polarization controllers 103 and 118; the operation control of the detector 125; the operation control of the DAQ 130; and the like.

As the control of the user interface 240, the main control unit 211 displays, on the display unit 240A, the observation image of the subject's eye E, the photographed image of the subject's eye E, the OCT image of the subject's eye E acquired using the OCT unit 100, the measurement result, the GUI, or the like. Further, the main control unit 211 receives the operation signal corresponding to the operation content of the user on the operation unit 240B, and controls each part of the ophthalmologic apparatus 1500b based on the received operation signal.

Further, the main control unit 211 can control the movement mechanism 150 for moving the entire optical system with respect to the subject's eye E.

For example, the main control unit 211 controls the LCD 39 to display the fixation target at a position on the screen of the LCD 39 corresponding the fixation position set manually or automatically. Moreover, the main control unit 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processing unit 230, for example.

The focusing driver 31A moves the photography focusing lens 31 in the direction along the optical axis of the imaging optical system 30, and moves the focus optical system 60 in the direction along the optical axis of the illumination optical system 10. This changes the focus position of the imaging optical system 30. The focusing driver 31A may include a dedicated mechanism for moving the photography focusing lens 31 and a dedicated mechanism for moving the focus optical system 60. The focusing driver 31A is controlled when performing focus adjustment or the like.

The focusing driver 43A moves the OCT focusing lens 43 in the optical axis direction of the measurement optical path. This changes the focus position of the measurement light LS. For example, the focus position of the measurement light LS can be arranged at the fundus Ef or near the fundus Ef by moving the OCT focusing lens 43 to the first lens position. For example, the focus position of the measurement light LS can be arranged at a far point position by moving the OCT focusing lens 43 to the second lens position. The focus position of the measurement light LS corresponds to the depth position (z position) of the beam waist of the measurement light LS.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction), a mechanism for moving it in the y direction (up-down direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main control unit 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described later to relatively move the optical system and subject's eye E so as to cancel the displacement of the subject's eye E with respect to the optical system. For example, the main control unit 211 controls the movement mechanism 150 to relatively move the optical system and the subject's eye E by outputting a control signal corresponding to the operation content with respect to the user interface 240 to the movement mechanism 150.

In the case of automatic alignment, the main control unit 211 controls the movement mechanism 150 to relatively move the optical system and the subject's eye E so as to cancel the displacement of the subject's eye E with respect to the optical system. In some embodiments, the main control unit 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main control unit 211 controls the fundus camera unit 2 etc. to control the fundus imaging (photography) and the anterior segment imaging. Further, the main control unit 211 controls the fundus camera unit 2 and the OCT unit 100 etc. to control the OCT measurement.

As in the conventional computer, the arithmetic control unit 200 includes a processor, RAM, ROM, hard disk drive, and communication interface, for example. A storage device such as the hard disk drive stores a computer program for controlling the ophthalmologic apparatus 1500b. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The fundus camera unit 2, the user interface 240, the OCT unit 100, and the arithmetic control unit 200 may be integrally provided (i.e., in a single housing), or they may be separately provided in two or more housings.

(Storage Unit 212)

The storage unit 212 stores various types of data. Examples of the data stored in the storage unit 212 include image data of an OCT image, image data of a fundus image, image data of an anterior segment image, and subject's eye information. The subject's eye information includes information on the subject such as patient ID and name, and information on the subject's eye such as identification information of the left eye/right eye.

In addition, the storage unit 212 stores various kinds of computer programs and data for operating the ophthalmologic apparatus 1500b.

The ophthalmologic apparatus 1500b is provided with the user interface 240 for accepting an operation from the user or presenting information to the user. The control unit 210 can control the user interface 240 to manage interface processing with the user.

(User Interface 240)

The user interface 240 includes the display unit 240A and the operation unit 240B. The display unit 240A includes the aforementioned display device of the arithmetic control unit 200 and the display apparatus 3. The operation unit 240B includes the aforementioned operation device of the arithmetic control unit 200. The operation unit 240B may include various types of buttons and keys provided on the case of the ophthalmologic apparatus 1500b or the outside. For example, when the fundus camera unit 2 has a case similar to that of the conventional fundus camera, the operation unit 240B may include a joy stick, an operation panel, and the like provided to the case. Further, the display unit 240A may include various kinds of display devices, such as a touch panel placed on the housing of the fundus camera unit 2.

It should be noted that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the control unit 210 as an electric signal. Moreover, operations and inputs of information may be performed using a graphical user interface (GUI) displayed on the display unit 240A and the operation unit 240B.

(Image Forming Unit 220)

The image forming unit 220 forms an OCT image (image data) of the subject's eye E based on the sampling data obtained by sampling the detection signal from the detector 125 using the DAQ 130. As with the conventional swept source OCT, the image formation process includes noise removal (noise reduction), filtering, dispersion compensation, fast Fourier transform (FFT), and the like. In the case of employing an OCT apparatus of another type, the image forming unit 220 performs known processing according to the type employed.

The image forming unit 220 that functions as above includes, for example, a microprocessor, RAM, ROM, a hard disk drive, a circuit board, and the like. In a storage device such as the hard disk drive, a computer program for causing the processor to execute the functions described above is stored in advance. It should be noted that "image data" and an "image" based on the image data may not be distinguished from each other in the present specification.

(Data Processing Unit 230)

The data processing unit 230 processes data acquired through photography of the subject's eye E or data acquired through OCT measurement.

The data processing unit 230 performs various kinds of image processing and various kinds of analysis processing on the image formed by the image forming unit 220. For example, the data processing unit 230 performs various types of image correction processing such as brightness correction. The data processing unit 230 performs various kinds of image processing and various kinds of analysis processing on images captured by the fundus camera unit 2 (e.g., fundus images, anterior segment images, etc.).

For example, the data processing unit 230 performs known image processing such as interpolation processing for interpolating pixels in tomographic images to form three-dimensional image data of the fundus Ef. Note that image data of a three-dimensional image means image data in which the positions of pixels are defined by a three-dimensional coordinate system. Examples of the image data of the three-dimensional image include image data defined by voxels three-dimensionally arranged. Such image data is referred to as volume data or voxel data. When displaying an image based on volume data, the data processing unit 230 performs rendering (volume rendering, maximum intensity projection (MIP), etc.) on the volume data, thereby forming image data of a pseudo three-dimensional image viewed from a particular line of sight. This pseudo three-dimensional image is displayed on the user interface 240 (display unit 240A).

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processing unit 230 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

The data processing unit 230 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processing unit 230 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processing unit 230 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processing unit 230 is also included in the OCT image.

Further, the data processing unit 230 performs predetermined analysis processing on the detection result of the interference light acquired by performing OCT measurement or the OCT image formed based on the detection result.

Examples of the predetermined analysis processing include specifying (identification) of a predetermined site (tissue, lesion) of the subject's eye E; calculation of a distance, area, angle, ratio, or density between designated sites (distance between layers, interlayer distance); calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic disc, a fovea, a macula, and the like. Examples of the predetermined lesion include a leukoma, a hemorrhage, and the like.

Further, the data processing unit 230 can perform phase stabilization processing on the OCT data (for example, three-dimensional complex OCT data, complex OCT volume data) obtained by performing OCT measurement so as to reduce the influence of the phase drift caused by the movement of the subject's eye and/or the phase instability in the OCT optical system 8.

For example, the image forming unit 220 or the data processing unit 230 forms an OCT image based on the absolute value of the complex OCT data on which the phase stabilization processing has been performed. Since the imaginary part of the complex OCT data can be used for imaging in addition to the real part of the complex OCT data, even higher definition OCT images can be obtained.

For example, the data processing unit 230 forms a phase image (phase information) and/or an OCTA image based on the absolute value of the complex OCT data on which the phase stabilization processing has been performed. Since the components affected by phase drift are removed from the imaginary part of the complex OCT data, phase images and OCTA images can be obtained with even higher accuracy.

Further, the data processing unit 230 can perform aberration correction processing for correcting the aberration caused by the subject's eye E or an optical system on the OCT data on which the phase stabilization processing has been performed.

Figure 7:
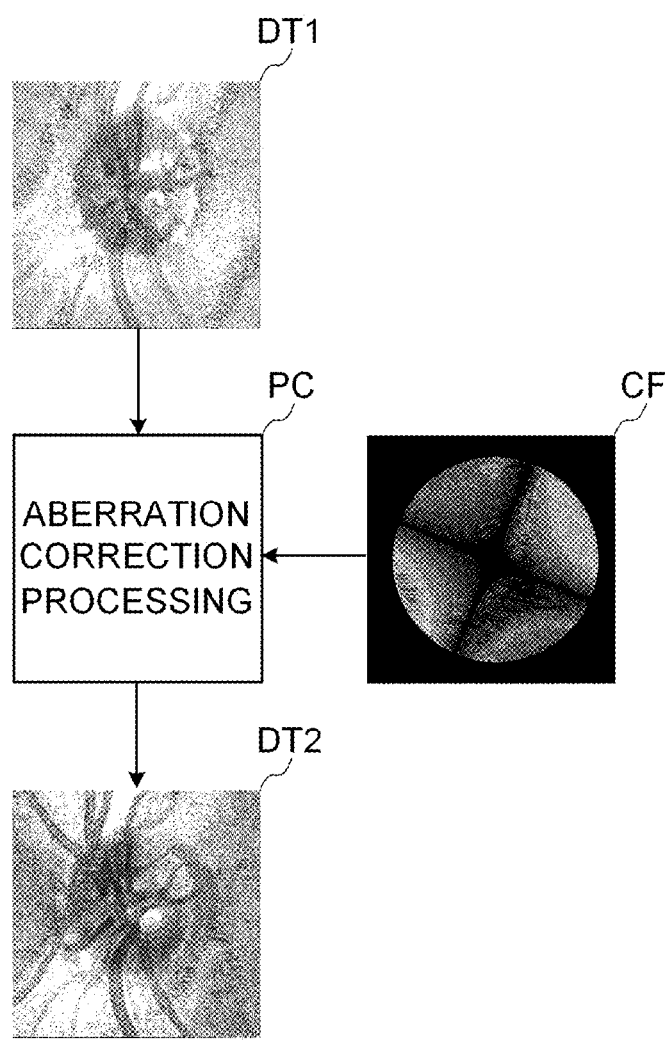
FIG. 7 is a schematic diagram for explaining processing performed by the ophthalmologic apparatus according to the embodiments.

FIG. 7 shows an operation diagram for explaining the aberration correction processing executed by the data processing unit 230.

First, the data processing unit 230 searches for parameter(s) of CAO filter CF as the filter information from the complex OCT data DT1 of the subject's eye E acquired by performing OCT measurement. Hereinafter, "search for parameter(s) of CAO filter" as the filter information may be referred to as "search for CAO filter".

Next, the data processing unit 230 performs aberration correction processing PC on the complex OCT data DT1 using the searched CAO filter CF to obtain the complex OCT data DT2 on which the aberration correction has been performed. In some embodiments, the aberration correction processing PC is performed in the frequency domain. In some embodiments, the aberration correction processing PC is performed in the space domain.

This allows to improve the accuracy of the OCT measurement result without being affected by the aberration caused by the subject's eye E or the optical system. This means improving the accuracy of the real part and the imaginary part of the complex OCT data on which the aberration correction has been performed. Thereby, the image quality of OCT images (including OCTA images) can be improved and the accuracy of phase between images can be improved.

Figure 8:
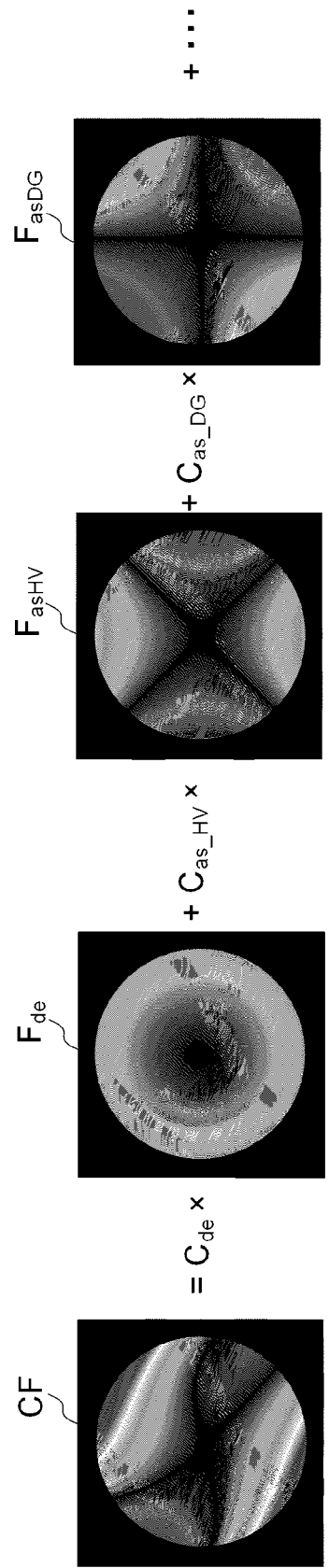
FIG. 8 is a schematic diagram for explaining processing performed by the ophthalmologic apparatus according to the embodiments.

FIG. 8 shows a diagram for explaining the CAO filter according to the embodiments.

The CAO filter can be represented by a Zernike polynomial corresponding to the distribution of wavefront aberrations on the pupil surface of the subject's eye E. The filter characteristics of the CAO filter can be adjusted by adjusted coefficient(s) (parameter(s)) of terms of each order of the Zernike polynomial.

The filter characteristics of the CAO filter are determined by synthesizing one or more filters corresponding to a predetermined distribution of wavefront aberrations according to the coefficients corresponding to each filter. In the embodiments, as shown in FIG. 8, the CAO filter CF is represented using the polynomial including a defocus term $F_{de}$, an astigmatism term $F_{asHV}$ in an HV direction (0-90 degree direction), and an astigmatism term $F_{asDG}$ in a diagonal direction (±45 degree direction). The CAO filter CF realizes desired filter characteristics by adjusting the coefficients $C_{de}$, $C_{as\_HV}$, and $C_{as\_DG}$ of each term as parameters. It should be noted that the CAO filter CF may include higher-order terms such as a coma term and a spherical aberration term.

Figure 9:
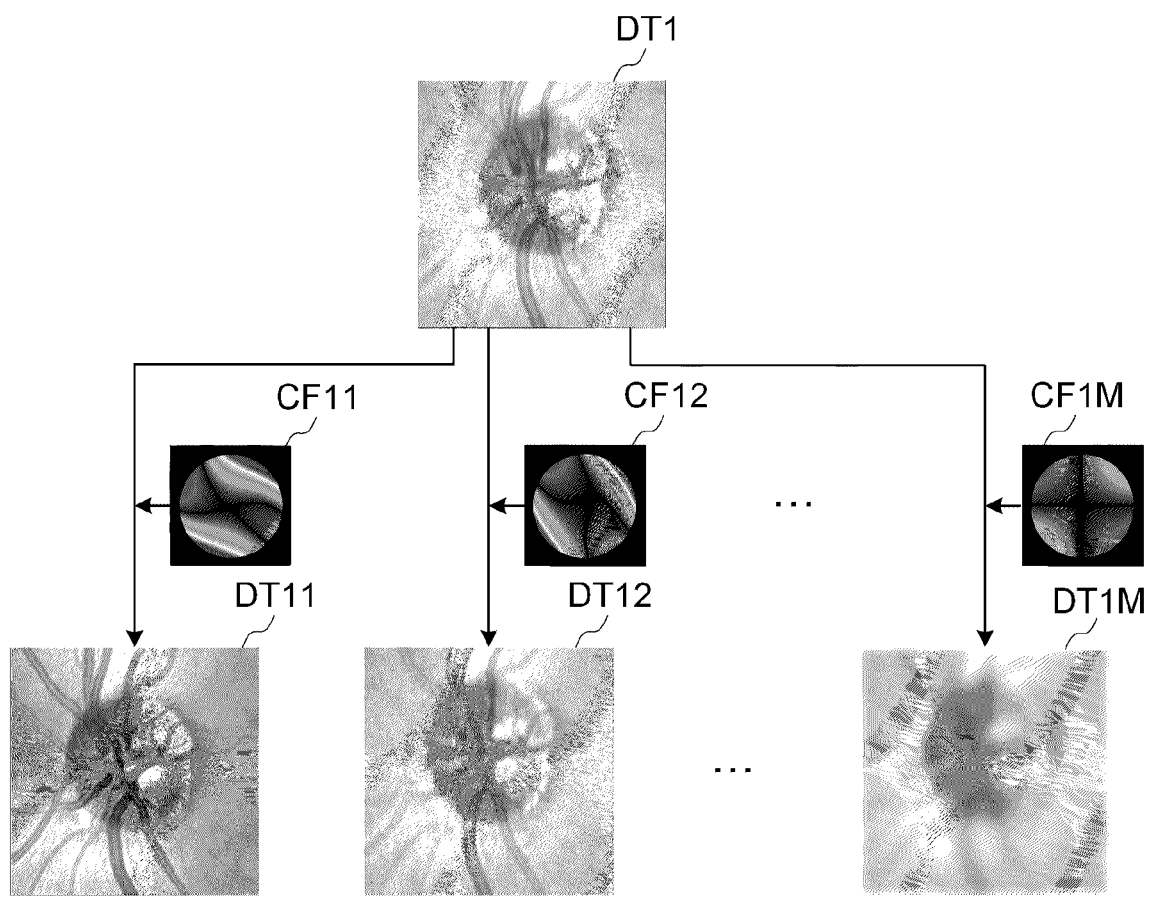
FIG. 9 is a schematic diagram for explaining processing performed by the ophthalmologic apparatus according to the embodiments.

FIG. 9 shows a diagram for explaining an example of the search processing of the CAO filter according to the embodiments.

The data processing unit 230 sequentially applies two or more CAO filters CF11, CF12, . . . , CF1M having different filter characteristics to the complex OCT data DT1 of the subject's eye E, and obtains two or more complex OCT data DT11, DT12, . . . , DT1M (M is an integer of 2 or more) on which the aberration correction has been performed. The data processing unit 230 evaluates the quality of each of the two or more acquired complex OCT data DT11 to DT1M, and specifies the CAO filter applied to the highest quality complex OCT data as the CAO filter of the search result.

Examples of method for evaluation the quality of the complex OCT data include a method for evaluating the image quality of the OCT image formed based on the complex OCT data. Examples of the OCT image include a tomographic image, a front image (projection image, en-face image), an OCTA image, and the like. For example, the data processing unit 230 can specify the complex OCT data having the highest quality based on the image quality evaluation value indicating the degree of the image quality of the formed OCT image.

In some embodiments, the data processing unit 230 can generate the parameter(s) (coefficient(s)) of the CAO filter described above from the refractive power information representing the refractive power of the subject's eye E. This allows to simplify or omit the search processing of the CAO filter (filter information).

Hereinafter, each part of the data processing unit 230 that realizes such a function will be described.

Figure 10:
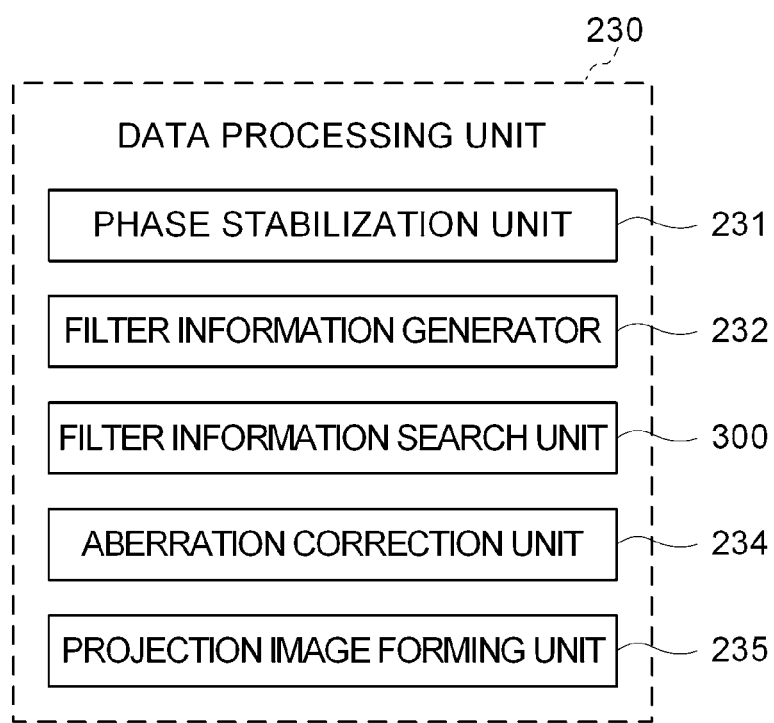
FIG. 10 is a schematic diagram illustrating an example of the configuration of a processing system of the ophthalmologic apparatus according to the embodiments.

FIG. 10 shows a block diagram of an example of the configuration of the data processing unit 230 of FIG. 6.

The data processing unit 230 includes a phase stabilization unit 231, a filter information generator 232, the filter information search unit 300, an aberration correction unit 234, and a projection image forming unit 235.

(Phase Stabilization Unit 231)

The phase stabilization unit 231 performs phase stabilization processing on the complex OCT data of the subject's eye E so as to cancel the influence of the phase drift caused by the movement of the subject's eye E to be measured and/or the phase instability in the system (OCT Optical System 8).

Figure 11:
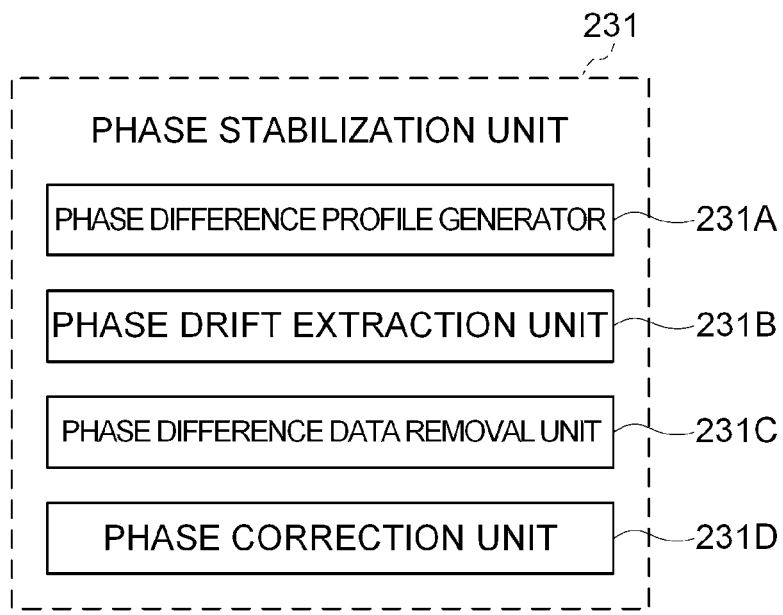
FIG. 11 is a schematic diagram illustrating an example of the configuration of a processing system of the ophthalmologic apparatus according to the embodiments.

FIG. 11 shows a block diagram of an example of the configuration of the phase stabilization unit 231 of FIG. 10.

The phase stabilization unit 231 includes a phase difference profile generator 231A, a phase drift extraction unit 231B, a phase difference data removal unit 231C, and a phase correction unit 231D.

(Phase Difference Profile Generator 231A)

The phase difference profile generator 231A generates the phase difference profile in which phase data representing the averaged phase difference for each A-line is arranged in the B-line direction from the three-dimensional complex OCT data. Specifically, the phase difference profile generator 231A calculates the phase difference for each depth position of A-line(s) between two adjacent B-frames of the complex OCT data, and averages the calculated phase differences in the depth direction (z direction), and generates the phase difference profile by arranging the phase differences, which are obtained by averaging, in the B-line direction.

Figure 12A:
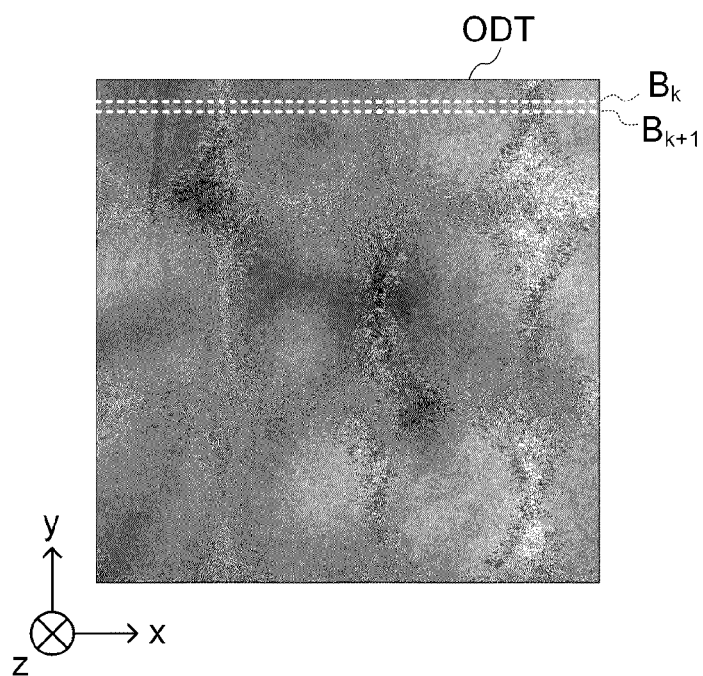
FIG. 12A is a schematic diagram for explaining processing performed by the ophthalmologic apparatus according to the embodiments.

FIG. 12A shows a diagram for explaining the operation of the phase difference profile generator 231A. FIG. 12A schematically shows the complex OCT data ODT with the horizontal direction as the x direction and the vertical direction as the y direction.

For example, the phase difference profile generator 231A integrates the phase differences, which are calculated for each depth position of A-line between two adjacent B-frames $B_k$ and $B_{k+1}$ as shown in Equation (1), in the z direction, averages the integrated phase differences, and obtains the phase difference for each A-line. The phase difference profile generator 231A similarly obtains the phase difference for each A-line between the next two B-frames $B_{k+1}$ and $B_{k+2}$. This is repeated sequentially, and the phase difference profile between the two B-frames is obtained sequentially for the three-dimensional complex OCT data ODT.

[Equation 1]

$$\Delta\varphi(B\#, A\#) = \text{angle}\left(\sum_z \overline{OCT(B\#-1, A\#, z)} \cdot OCT(B\#, A\#, z)\right) \quad (1)$$

(Phase Drift Extraction Unit 231B)

The phase drift extraction unit 231B extracts the phase drift from the phase difference profile generated by the phase difference profile generator 231A. Specifically, the phase drift extraction unit 231B extracts the phase drift by performing at least one of smoothing processing, polynomial fitting, and high frequency cut filtering processing on the phase difference profile.

Figure 12B:
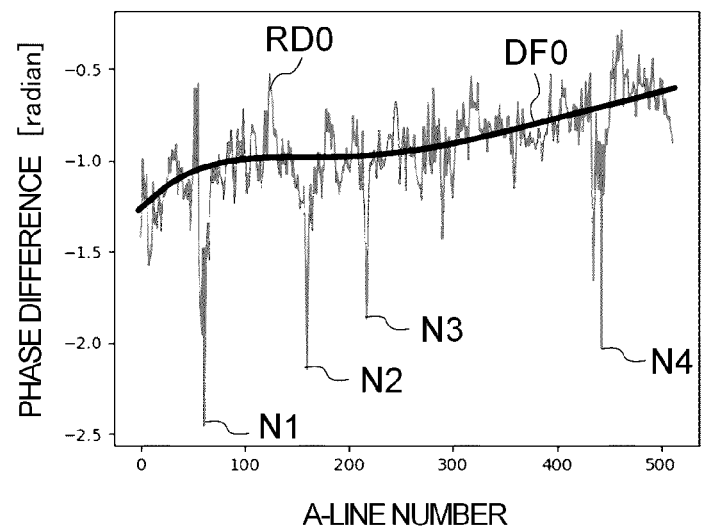
FIG. 12B is a schematic diagram for explaining processing performed by the ophthalmologic apparatus according to the embodiments.

FIG. 12B shows a diagram for explaining the operation of the phase drift extraction unit 231B. In FIG. 12B, the horizontal axis represents the A-line number corresponding to the A-line position (the incident position of the measurement light scanned in the B scan direction), and the vertical axis represents the phase difference.

For example, the phase drift extraction unit 231B extracts the phase drift DF0 by performing smoothing processing on the phase difference profile RD0 generated by the phase difference profile generator 231A.

A parameter of at least one of the smoothing processing, the polynomial fitting, and the high frequency cut filtering processing which are performed by the phase drift extraction unit 231B is set based on at least one of a frequency of phase change in the OCT optical system 8 for acquiring the complex OCT data ODT, a speed of the phase change, and time required for an OCT scan in the OCT optical system 8.

(Phase Difference Data Removal Unit 231C)

The phase difference data removal unit 231C removes less reliable phase difference data from the phase difference profile generated by the phase difference profile generator 231A before extracting the phase drift described above. The phase drift extraction unit 231B extracts the phase drift from the phase difference profile from which the less reliable phase difference data is removed by the phase difference data removal unit 231C. This allows to obtain the phase drift from which a local phase difference change has been removed.

Figure 13:
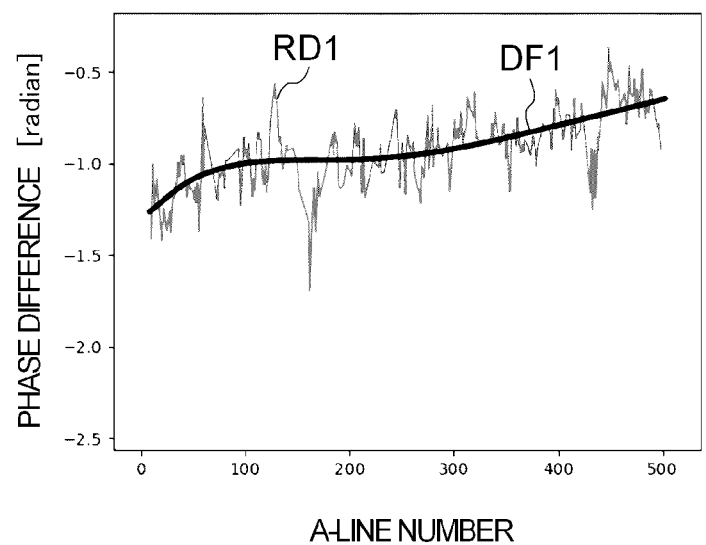
FIG. 13 is a schematic diagram for explaining processing performed by the ophthalmologic apparatus according to the embodiments.

FIG. 13 shows a diagram for explaining the operation of the phase difference data removal unit 231C. Similarly to FIG. 12B, in FIG. 13, the horizontal axis represents the A-line number corresponding to the A-line position, and the vertical axis represents the phase difference.

For example, the phase difference data removal unit 231C removes (decimates) the less reliable phase difference data N1 to N4 from the phase difference profile RD0 shown in FIG. 12B, and generates the phase difference profile RD1 shown in FIG. 13. The phase drift extraction unit 231B extracts the phase drift DF1 from the phase difference profile RD1 shown in FIG. 13. Thus, as compared with the phase drift DF0, the influence of local phase change (local error) can be suppressed.

Examples of the less reliable data include phase difference data with weak signal strength, and phase difference data in which the contribution of the phase difference data at a specific depth position is large in the phase difference calculation process (averaging process) of Equation (1). The phase difference data with weak signal may reduce the high reliability that the phase difference data with strong signal strength has. The phase difference data with a large contribution in the phase difference calculation process of Equation (1) is more likely to break the assumption that the expected value of the phase difference will be zero.

For example, the phase difference data removal unit 231C specifies the phase difference data that satisfies Equation (2) as data whose signal strength is less than a predetermined threshold level, and removes the specified data from the phase difference profile.

[Equation 2]

$$\sum_z \text{abs}\left(\overline{OCT(B\#-1, A\#, z)} \cdot OCT(B\#, A\#, z)\right) < I_{th} \quad (2)$$

For example, the phase difference data removal unit 231C specifies the phase difference data that satisfies Equation (3) as data whose contribution of the phase difference at a predetermined depth position exceeds a predetermined threshold in the averaging process when calculating the phase difference in Equation (1), and removes the specified data from the phase difference profile.

[Equation 3]

$$\frac{\max\left[\text{abs}\left(\overline{OCT(B\#-1, A\#, z)} \cdot OCT(B\#, A\#, z)\right)\right]_z}{\sum_k \text{abs}\left(\overline{OCT(B\#-1, A\#, z)} \cdot OCT(B\#, A\#, z)\right)} < r_{th} \quad (3)$$

The phase difference data removal unit 231C can remove at least one of the following from the phase difference profile as the less reliable data: data whose signal strength is less than a predetermined threshold level, and data whose contribution of the phase difference at a predetermined depth position exceeds a predetermined threshold level in the averaging process.

(Phase Correction Unit 231D)

The phase correction unit 231D corrects the phase of the complex OCT data of either one of the above two B-frames for which the phase difference profile has been generated, based on the phase drift extracted by the phase drift extraction unit 231B.

For example, when performing phase correction between B-frames $B_k$ and $B_{k+1}$ shown in FIG. 12A, the phase correction unit 231D multiplies $\exp(-i\varphi)$ to the complex OCT data of B-frame $B_{k+1}$ in the frequency domain using the phase difference $\varphi$ in the phase drift for each A-line. In some embodiments, the phase correction unit 231D performs convolution operation on the complex OCT data in space domain.

For example, the phase stabilization unit 231 sequentially performs the above phase correction processing on the B-frames of the three-dimensional complex OCT data. That is, the phase stabilization unit 231 is configured to correct the phase of the complex OCT data of a second B-frame based on the phase difference profile generated by the phase difference profile generator 231A for a first B-frame and the second B-frame adjacent to each other, and then to correct the phase of the complex OCT data of a third B-frame based on the phase difference profile generated by phase difference phase difference profile generator 231A for the second B-frame and the third B-frame adjacent to the second B-frame.

(Filter Information Generator 232)

The filter information generator 232 shown in FIG. 10 generates the parameter(s) of the CAO filter for applying to the complex OCT data of the subject's eye E, as the filter information. In the example shown in FIG. 8, the parameter(s) of the CAO filter is/are the coefficient(s) of each term of the Zernike polynomial.

The filter information generator 232 generates the parameter(s) of the CAO filter, which is/are the initial value(s) of the search processing, as the filter information. For example, the filter information generator 232 acquires the filter information by referring to the initial value(s) of the parameter(s) of the CAO filter stored in advance in the storage unit 212.

In some embodiments, the filter information generator 232 generates the parameter(s) of the CAO filter as the filter information from the refractive power information of the subject's eye E acquired by the refractive power measuring for the subject's eye E performed by the external ophthalmologic apparatus. That is, the filter information generator 232 can generates the filter information based on the refractive power information of the subject's eye E, as a reference filter information. The parameter(s) of the CAO filter is/are searched so that the quality of the complex OCT data becomes a predetermined level based on the generated reference filter information.

The equivalent spherical power SE, the spherical power S, the astigmatic power C, and the astigmatic axis angle A can be calculated from Equations (4) to (7) using the coefficients of each term of the Zernike polynomial.

[Equation 4]

$$SE = S_{move} - 4 \times \frac{c_2^0}{r^2} \quad (4)$$

$$S = SE - \frac{1}{2} \times C \quad (5)$$

$$C = -4 \times \frac{\sqrt{(c_2^{-2})^2 + (c_2^2)^2}}{r^2} \quad (6)$$

$$A = \tan^{-1}\left(\frac{c_2^{-2}}{c_2^2}\right) \times \frac{1}{2} \times \frac{180}{\pi} + 90 \quad (7)$$

In Equation (4), $S_{move}$ represents the spherical power of the fixation movement, r represents the pupil diameter, and $c_2^0$ represents the coefficient of the defocus term (corresponding to the coefficient $C_{de}$ in FIG. 8). Further, in Equations (6) and (7), $c_2^{-2}$ represents the coefficient of the astigmatism term in the DG direction (corresponding to the coefficient $C_{as\_DG}$ in FIG. 8), and $c_2^2$ represents the coefficient of the astigmatism term in the HV direction (corresponding to the coefficient $C_{as\_HV}$ in FIG. 8).

When the coefficient is a RMS (Root mean Square) value, the equivalent spherical power SE, the spherical power S, the astigmatic power C, and the astigmatic axis angle A can be calculated from Equations (8) to (11).

[Equation 5]

$$SE = S_{move} - 4\sqrt{3} \times \frac{c_2^0}{r^2} \quad (8)$$

$$S = SE - \frac{1}{2} \times C \quad (9)$$

$$C = -4\sqrt{6} \times \frac{\sqrt{(c_2^{-2})^2 + (c_2^2)^2}}{r^2} \quad (10)$$

$$A = \tan^{-1}\left(\frac{c_2^{-2}}{c_2^2}\right) \times \frac{1}{2} \times \frac{180}{\pi} + 90 \quad (11)$$

According to Equations (4) to (7) or Equations (8) to (11), the filter information generator 232 can calculate the coefficient of each term of the Zernike polynomial from the refractive power information of the subject's eye E to generate the parameters of the CAO filter as the filter information.

(Filter Information Search Unit 300)

The filter information search unit 300 searches for the filter information for correcting the aberration in the complex OCT data of a subject's eye E so that the quality of the complex OCT data becomes a predetermined level. Specifically, the filter information search unit 300 repeats the evaluation of the quality of the complex OCT data, on which has been corrected based on the filter information, and the update of the filter information, so that the quality of the complex OCT data becomes the predetermined level. Further, the filter information search unit 300 can roughly search for the filter information by repeating the evaluation of the quality and the update of the filter information, and can finely search for the filter information by repeating the update of the filter information and the evaluation of the quality within a search range searched roughly.

Figure 14:
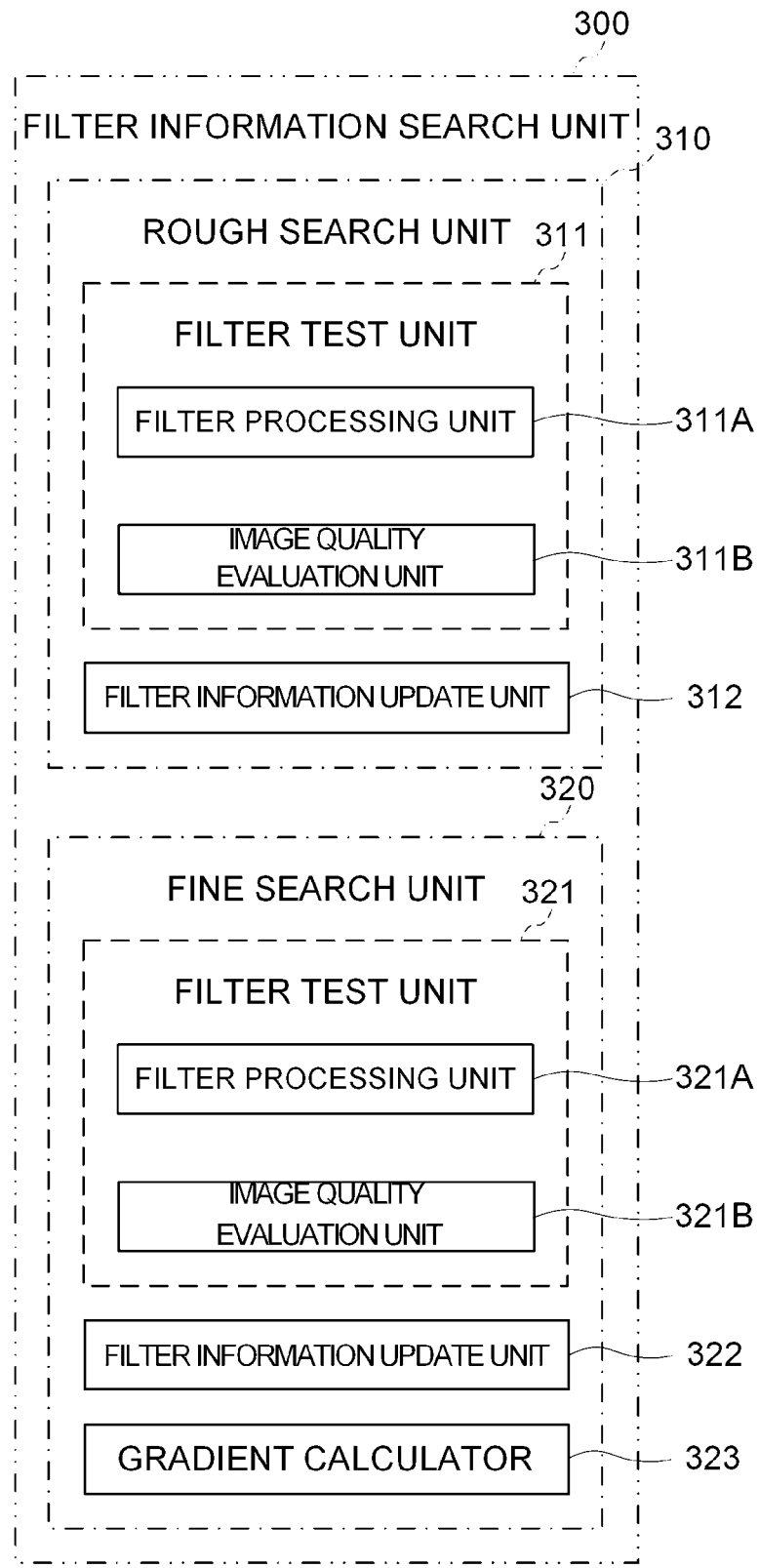
FIG. 14 is a schematic diagram illustrating an example of the configuration of a processing system of the ophthalmologic apparatus according to the embodiments.

FIG. 14 shows a block diagram of a configuration example of a filter information search unit 300 in FIG. 10. The filter information search unit 300 includes a rough search unit 310 and a fine search unit 320.

(Rough Search Unit 310)

The rough search unit 310 roughly searches for the filter information by repeating the evaluation of the quality of the complex OCT data and the update of the filter information. Such the rough search unit 310 includes a filter test unit 311 and a filter information update unit 312.

(Filter Test Unit 311)

The filter test unit 311 applies the CAO filter to the complex OCT data, and evaluates the quality of the complex OCT data in which the aberration has been corrected. Such the filter test unit 311 includes a filter processing unit 311A and an image quality evaluation unit 311B.

(Filter Processing Unit 311A)

The filter processing unit 311A performs filter processing on the complex OCT data by a known method using the CAO filter during the rough search processing. For example, the filter processing unit 311A multiplies the complex OCT data in the frequency domain by exp HO corresponding to the parameters of the CAO filter. For example, the filter processing unit 311A performs convolution operation on the complex OCT data in space domain using the filter coefficients corresponding to the parameters of the CAO filter.

(Image Quality Evaluation Unit 311B)

The image quality evaluation unit 311B evaluates the image quality of the OCT image (fundus image) formed based on the complex OCT data in which the aberration has been corrected by the filter processing unit 311A. For example, the OCT image is formed by the image forming unit 220.

The image quality evaluation unit 311B can calculate the image quality evaluation value of the OCT image. The image quality evaluation value is a numerical value indicating the degree of image quality of the OCT image, and is used for evaluating whether or not the image quality is good.

The image quality evaluation value may be any kind of value that can be calculated by any method. A typical image quality evaluation value is represented by a signal-to-noise ratio (S/N ratio) for two types of image regions in an OCT image. A specific example of the image quality evaluation value is an S/N ratio relating to a signal in an image region representing a site of the eye and noise in an image region representing a background that is not the site of the eye. The image region representing the site of the eye is called a signal region, and the image region representing the background is called a background region.

The method of calculating the image quality evaluation value expressed as the S/N ratio for the signal region and the background region is arbitrary. A specific example thereof will be described below.

First, the image quality evaluation unit 311B specifies a pixel with the maximum luminance and a pixel with minimum luminance for each of a plurality of A-scan images constituting the OCT image. Next, the image quality evaluation unit 311B creates a histogram of the luminance value based on the luminance value of the pixel group (for example, 40 pixels before and after) in a predetermined range including the specified pixel with the maximum luminance. Similarly, the image quality evaluation unit 311B creates a histogram of the luminance value based on the luminance value of the pixel group in a predetermined range including the specified pixel with minimum luminance.

Subsequently, the image quality evaluation unit 311B searches for the maximum position (luminance value) whose frequency value exceeds 0, in the histogram corresponding to the pixel group including the pixel with the minimum luminance. Further, in the histogram corresponding to the pixel group including the pixel with the maximum luminance, the total number of pixels (N) included in the range of the luminance value searched above or less and the total number of pixels (S) included in the 255th luminance value from the top of the searched luminance value are obtained. Then, the image quality evaluation unit 311B evaluates what percentage of the whole the portion that can be regarded as a signal (that is, the portion that can be regarded as not noise) in the image is evaluated by the following arithmetic expression: $100 \times S \div (S+N)$. The image quality evaluation unit 311B applies such a series of operations to each A-scan image to obtain a plurality of numerical values corresponding to the plurality of A-scan images. Then, the image quality evaluation unit 311B obtains the average value of these numerical values and uses this as the image quality evaluation value.

(Filter Information Update Unit 312)

The filter information update unit 312 updates the parameter(s) of the CAO filter searched by the rough search unit 310, by increasing the parameter(s) by a predetermined increase or by decreasing the parameter(s) by a predetermined decrease. The increase or decrease may be different depending on the type of parameter(s), or it may be common to two or more types of parameters. In some embodiments, the filter information update unit 312 updates one of the parameters of the CAO filter alone. In some embodiments, the filter information update unit 312 updates two or more parameters of the CAO at the same time.

As described above, in the rough search unit 310, the filter test unit 311 obtains the complex OCT data in which the aberration has been corrected by applying a CAO filter in the filter processing unit 311A, for example, in the frequency domain. After that, the filter test unit 311 evaluates the image quality of the OCT image formed based on the complex OCT data in the image quality evaluation unit 311B, in the space domain. The rough search unit 310 roughly searches for the CAO filter by repeating the update of the parameter(s) of the CAO filter by the filter information update unit 312 and the evaluation of the image quality by the filter test unit 311.

(Fine Search Unit 320)

The fine search unit 320 finely searches for the filter information, by repeating the update of the filter information and the evaluation of the quality within a search range searched by the rough search unit 310. Such the fine search unit 320 includes a filter test unit 321 and a filter information update unit 322, and a gradient calculator 323.

(Filter Test Unit 321)

The filter test unit 321 applies the CAO filter to the complex OCT data, and evaluates the quality of the complex OCT data in which the aberration has been corrected, in the same manner as the filter test unit 311. Such the filter test unit 321 includes a filter processing unit 321A and an image quality evaluation unit 321B.

(Filter Processing Unit 321A)

The filter processing unit 321A performs filter processing on the complex OCT data by a known method using the CAO filter during the fine search processing. The processing performed by the filter processing unit 321A is the same as the processing performed by the filter processing unit 311A.

(Image Quality Evaluation Unit 321B)

The image quality evaluation unit 321B evaluates the image quality of the OCT image (fundus image) formed based on the complex OCT data in which the aberration has been corrected by the filter processing unit 321A. The image quality evaluation unit 321B can calculate the image quality evaluation value of the OCT image, in the same manner as the image quality evaluation unit 311B.

(Filter Information Update Unit 322)

The filter information update unit 322 updates the parameter(s) of the CAO filter searched by the fine search unit 320, by increasing or decreasing the parameter(s). The filter information update unit 322 can update the parameter(s) of the CAO filter in accordance with a gradient calculated by the gradient calculator 323 described later. In some embodiments, the filter information update unit 322 updates one of the parameters of the CAO filter alone. In some embodiments, the filter information update unit 322 updates two or more parameters of the CAO at the same time.

(Gradient Calculator 323)

The gradient calculator 323 calculates the gradient of the image quality evaluation value calculated by the image quality evaluation unit 321B.

For example, the gradient calculator 323 calculates the gradient of the image quality evaluation value changing with the update of the filter information. The filter information update unit 322 updates the filter information based on the gradient of the image quality evaluation value calculated by the gradient calculator 323. Specifically, the filter information update unit 322 updates the filter information so that the more gradual the gradient of the calculated image quality evaluation value is, the smaller the increase or decrease becomes, and that the steeper the gradient is, the larger the increase or decrease becomes.

As described above, in the fine search unit 320, the filter test unit 321 obtains the complex OCT data in which the aberration has been corrected by applying a CAO filter in the filter processing unit 321A, for example, in the frequency domain. After that, the filter test unit 321 evaluates the image quality of the OCT image formed based on the complex OCT data in the image quality evaluation unit 321B, in the space domain. In the fine search unit 320, the gradient calculator 323 calculates the gradient of the image quality evaluation value changing with the update of the filter information, and the filter information update unit 322 updates the filter information based on the calculated gradient of the image quality evaluation value. The fine search unit 320 finely searches for the CAO filter by repeating the update of the parameter(s) of the CAO filter by the filter information update unit 322 according to the gradient of the image quality evaluation value and the evaluation of the image quality by the filter test unit 321.

(Aberration Correction Unit 234)

The aberration correction unit 234 shown in FIG. 10 corrects the aberration in the complex OCT data of the subject's eye E, based on the CAO filter (parameter(s)) searched by the filter information search unit 300. The aberration correction unit 234 performs filter processing on the complex OCT data by a known method using the CAO filter. For example, the aberration correction unit 234 multiplies the complex OCT data in the frequency domain by exp $(-i\varphi')$ corresponding to the parameters of the CAO filter. For example, the aberration correction unit 234 performs convolution operation on the complex OCT data in space domain using the filter coefficients corresponding to the parameters of the CAO filter.

At least one of the functions of the filter processing unit 311A and the filter processing unit 321A may be realized by the aberration correction unit 234.

(Projection Image Forming Unit 235)

The projection image forming unit 235 forms the projection image based on the complex OCT data of the subject's eye E. For example, the projection image forming unit 235 forms the projection image based on the complex OCT data in which the aberration has been corrected by the aberration correction unit 234.

The projection image forming unit 235 forms the projection image by projecting the three-dimensional image of the subject's eye E in the z direction. For example, the projection image is used to judge the quality of the complex OCT data.

In the ophthalmologic apparatus 1500b having the above configuration, the main control unit 211 according to the embodiments can display, on the display unit 240A, the aberration information on the pupil surface of the subject's eye E corresponding to the parameter(s) of the searched CAO filter, as the display control unit. The aberration information includes at least one of the information representing the refractive power, Zernike coefficient, and the distribution information (wavefront aberration information) of phase shift of light. The information representing the refractive power includes at least one of the equivalent spherical power (SE), the spherical power (S), the astigmatic power (C), and the astigmatic axis angle (A).

The data processing unit 230 that functions as above includes, for example, a processor described above, a RAM, a ROM, a hard disk drive, a circuit board, and the like. In a storage device such as the hard disk drive, a computer program for causing the processor to execute the functions described above is stored in advance.

The ophthalmologic information processing apparatus 1200, the ophthalmologic information processing unit 1200a, 1200b, or the data processing unit 230 is an example of the "ophthalmologic information processing apparatus" according to the embodiments. The phase difference profile generator 231A is an example of the "generator" according to the embodiments. The phase drift extraction unit 231B is an example of the "extractor" according to the embodiments. The phase difference data removal unit 231C is an example of the "removal unit" according to the embodiments. The image forming unit 220 or the data processing unit 230 is an example of the "image forming unit" according to the embodiments. The OCT optical system 1101 or the OCT optical system 8 is an example of the "measurement system" according to the embodiments.

[Operation]

The operation of the ophthalmologic apparatus 1500b according to the embodiments will be described.

Figure 15:
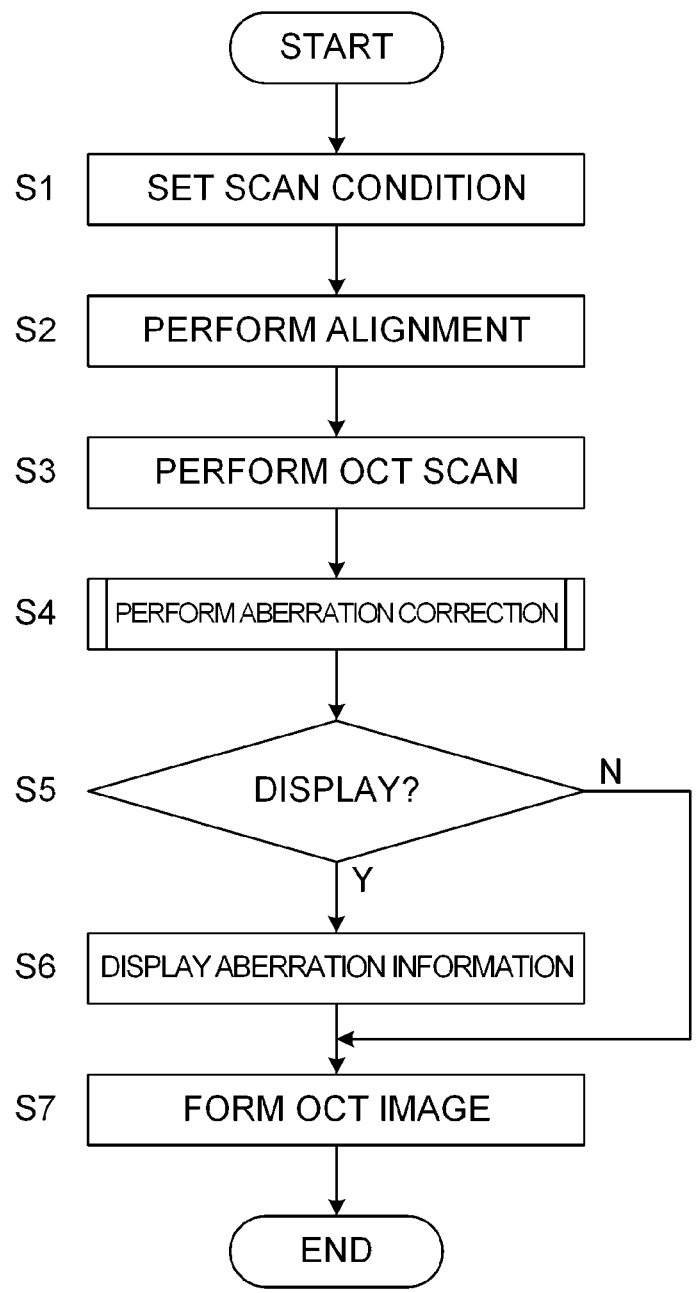
FIG. 15 is a flowchart illustrating an example of an operation of the ophthalmologic apparatus of the embodiments.
Figure 16:
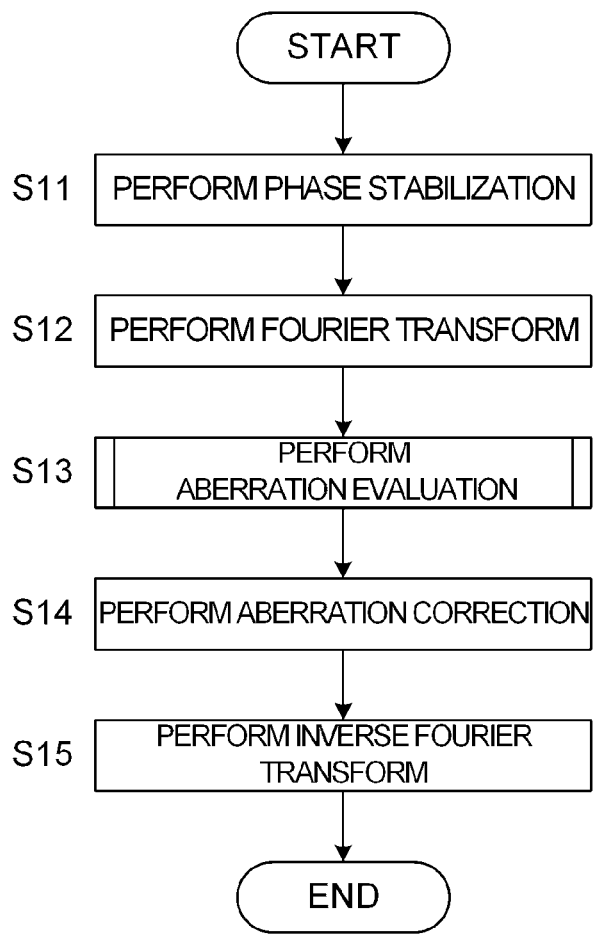
FIG. 16 is a flowchart illustrating an example of an operation of the ophthalmologic apparatus of the embodiments.
Figure 17:
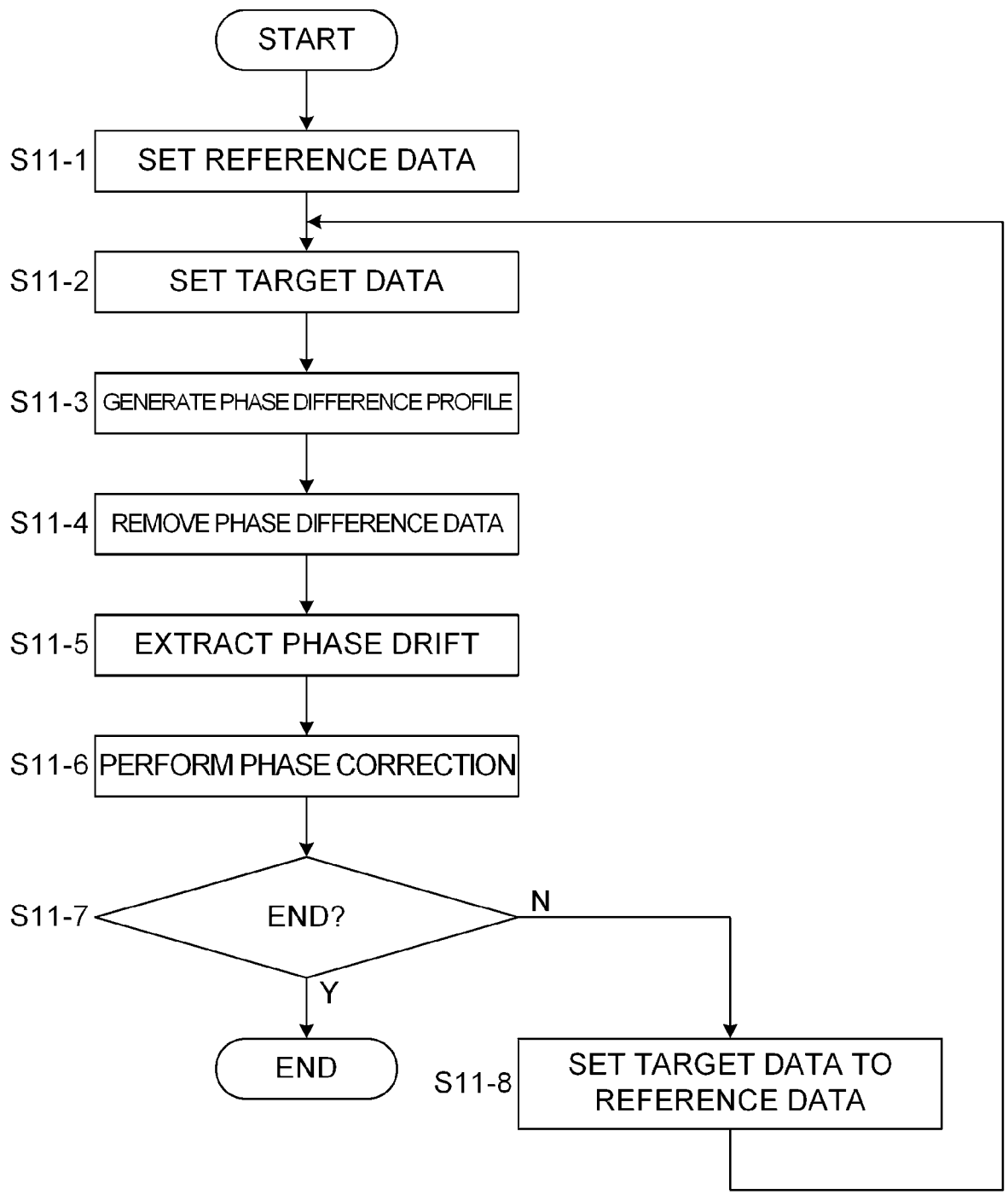
FIG. 17 is a flowchart illustrating an example of an operation of the ophthalmologic apparatus of the embodiments.
Figure 18:
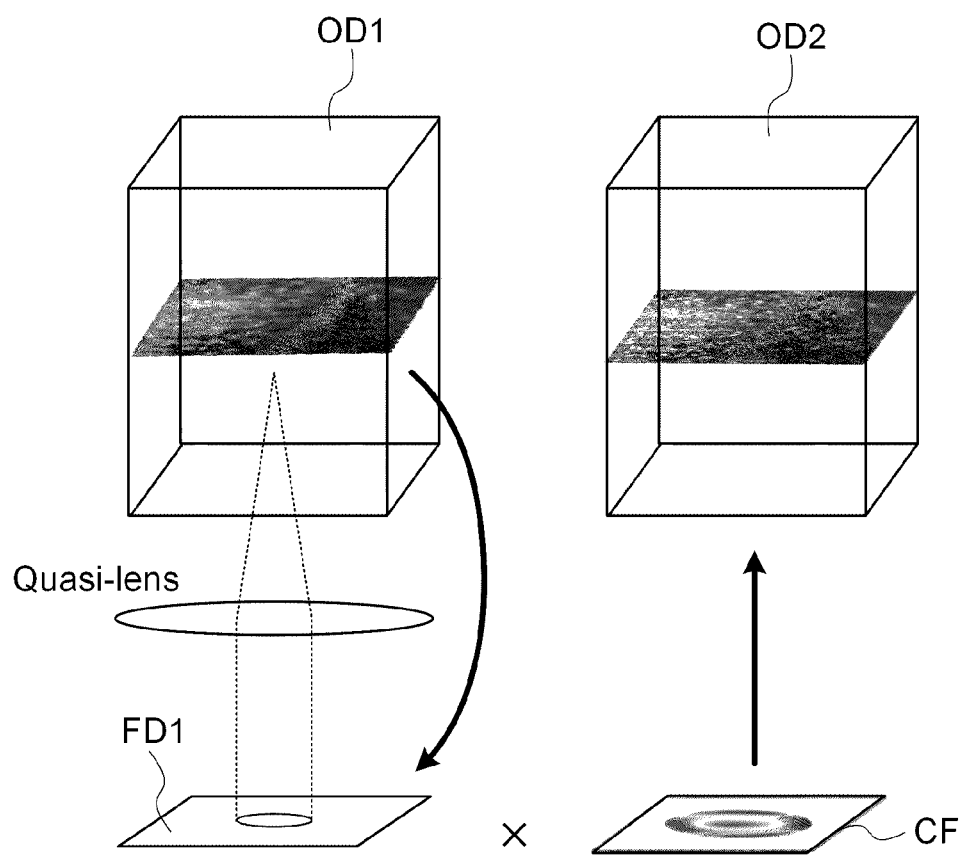
FIG. 18 is a schematic diagram for explaining processing performed by the ophthalmologic apparatus according to the embodiments.
Figure 19:
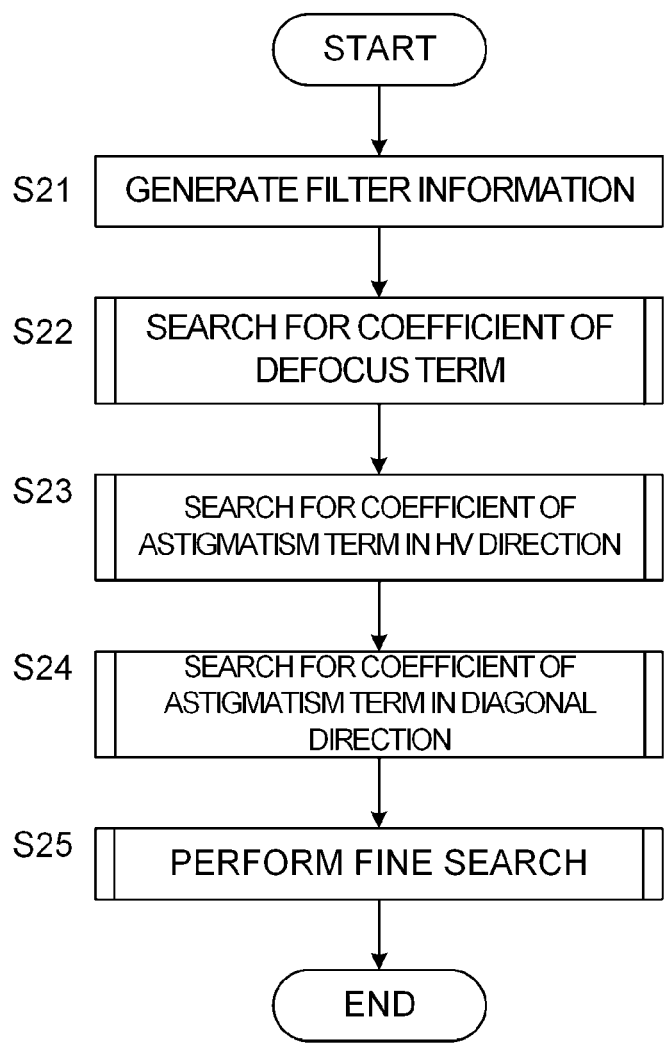
FIG. 19 is a flowchart illustrating an example of an operation of the ophthalmologic apparatus of the embodiments.
Figure 20:
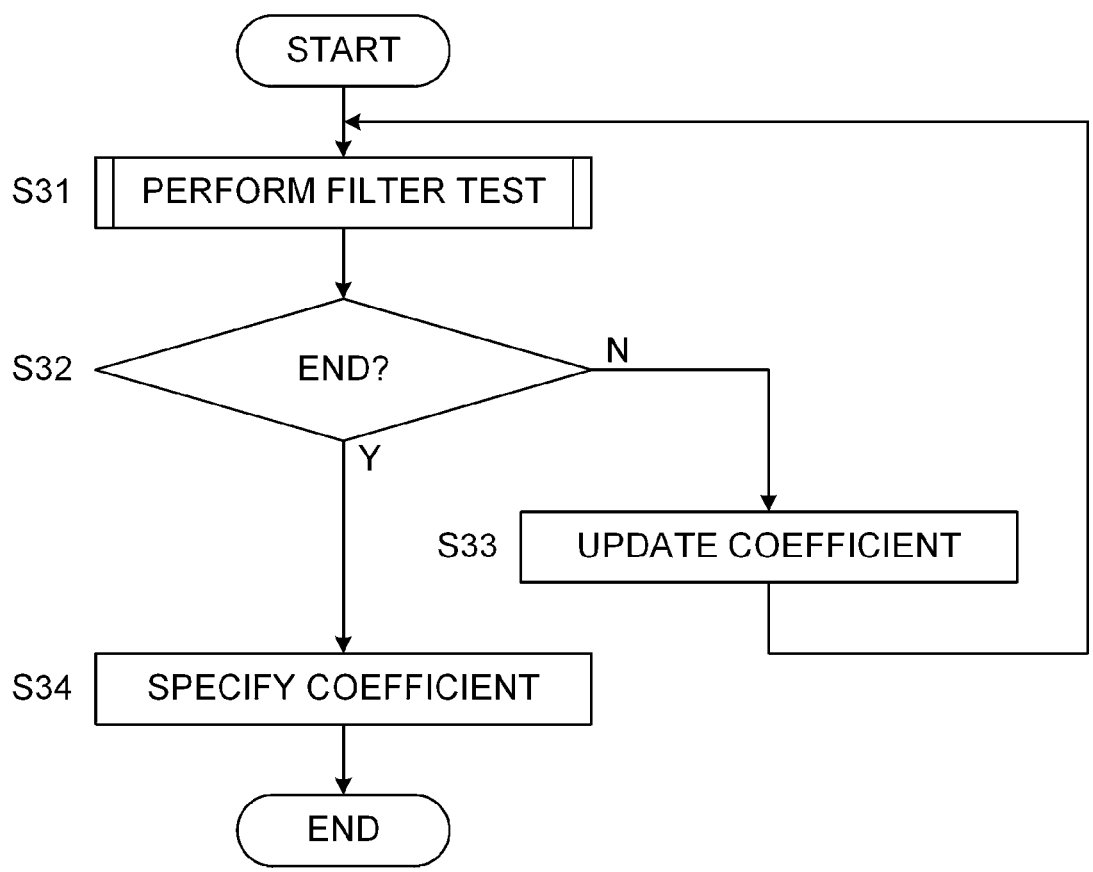
FIG. 20 is a flowchart illustrating an example of an operation of the ophthalmologic apparatus of the embodiments.
Figure 21:
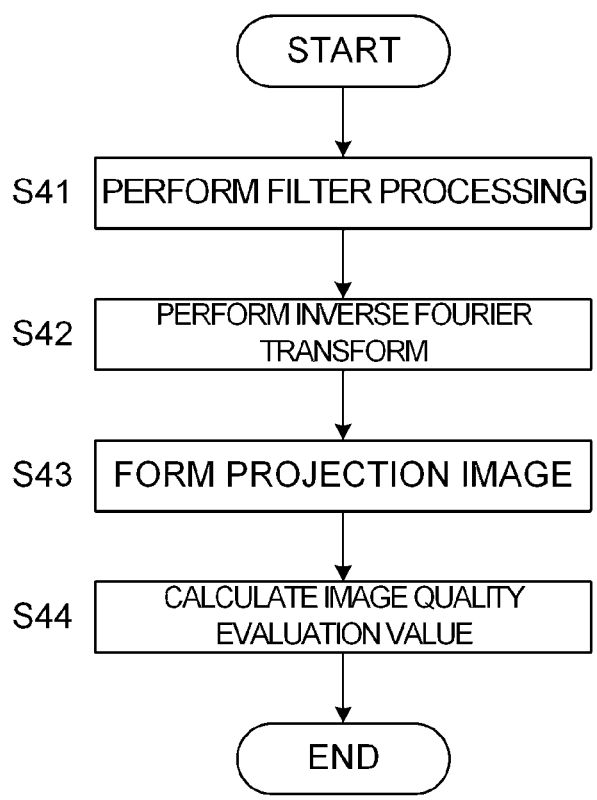
FIG. 21 is a flowchart illustrating an example of an operation of the ophthalmologic apparatus of the embodiments.
Figure 22:
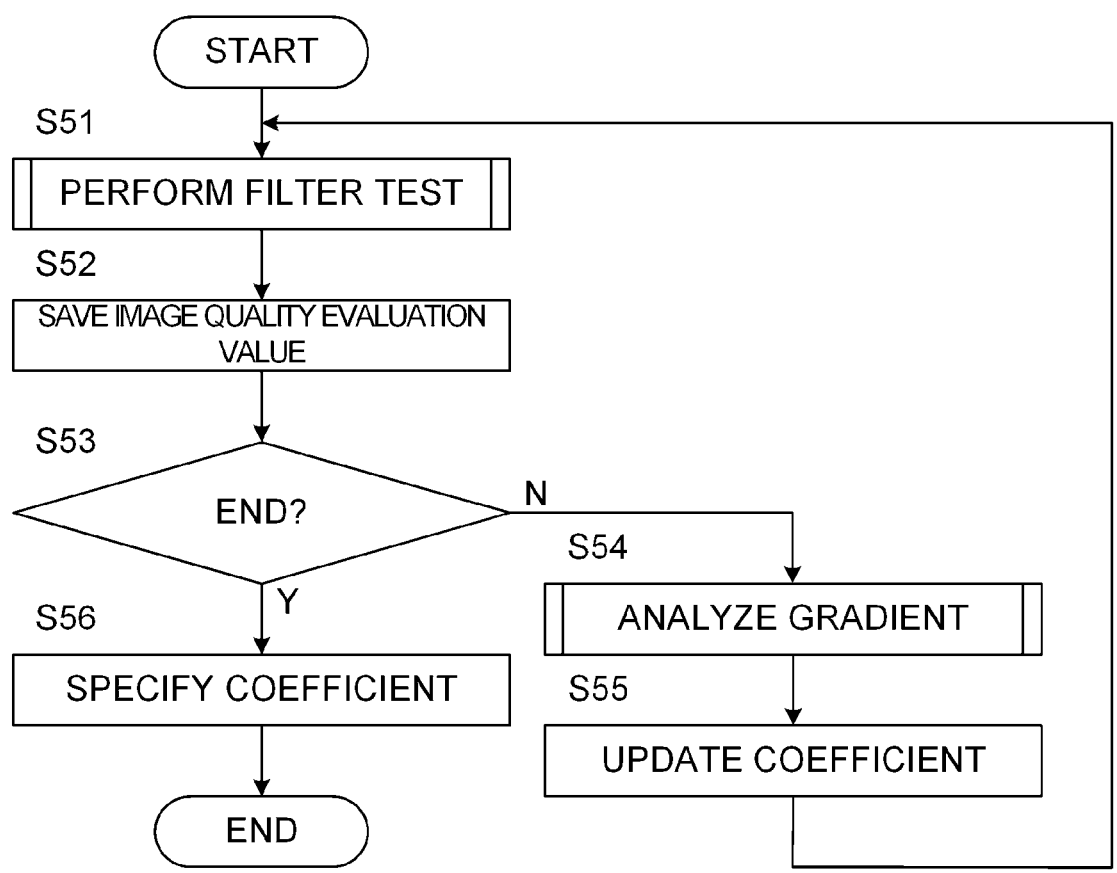
FIG. 22 is a flowchart illustrating an example of an operation of the ophthalmologic apparatus of the embodiments.
Figure 23:
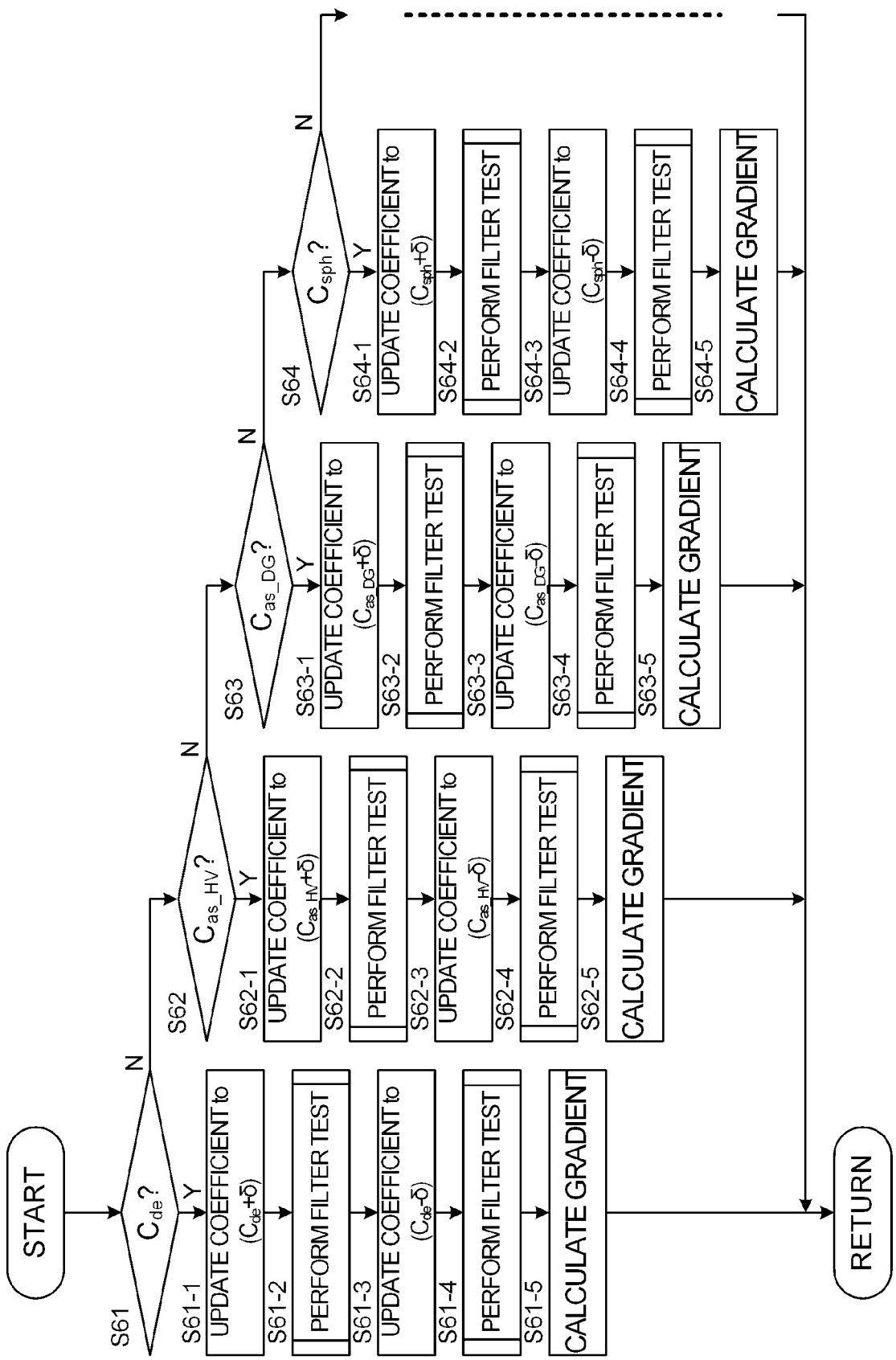
FIG. 23 is a flowchart illustrating an example of an operation of the ophthalmologic apparatus of the embodiments.

FIGS. 15 to 23 show examples of the operation of the ophthalmologic apparatus 1500b according to the embodiments. FIGS. 15 to 17, and 19 to 23 show flowcharts of the examples of the operation of the ophthalmologic apparatus 1500b according to the embodiments. FIG. 16 shows a flowchart of an example of the operation of step S4 in FIG. 15. FIG. 17 shows a flowchart of an example of the operation of step S11 in FIG. 16. FIG. 19 shows a flowchart of an example of the operation of step S13 in FIG. 16. FIG. 20 shows a flowchart of an example of each operation of steps S22 to S24 in FIG. 19. FIG. 21 shows a flowchart of an example of the operation of step S31 in FIG. 20. FIG. 22 shows a flowchart of an example of the operation of step S25 in FIG. 19. FIG. 23 shows a flowchart of an example of the operation of step S54 in FIG. 22. The storage unit 212 stores computer programs for realizing the processing shown in FIGS. 15 to 17 and 19 to 23. The main control unit 211 operates according to the computer programs, and thereby the main control unit 211 performs the processing shown in FIGS. 15 to 17 and 19 to 23. FIG. 18 shows a diagram for explaining the operation of steps S12 to S15 in FIG. 16.

(S1: Set Scan Condition)

First, the main control unit 211 accepts designation of a scan condition from the user.

The user can designate a scan mode and a scan range by operating the operation unit 240B. When the scan mode and the scan range are designated by operating the operation unit 240B by the user, the main control unit 211 analyzes an operation information from the operation unit 240B to specify the designated scan mode and the designated scan range.

In some embodiments, the main control unit 211 sets at least one of the scan mode and the scan range corresponding to an operation mode based on the operation mode designated by the user.

(S2: Perform Alignment)

Next, the main control unit 211 performs alignment.

For example, the main control unit 211 controls the alignment optical system 50 to project the alignment indicator onto the subject's eye E. At this time, a fixation target generated by the LCD 39 is also projected onto the subject's eye E. The main control unit 211 controls the movement mechanism 150 based on the movement amount of the optical system to relatively to move the optical system with respect to the subject's eye E by the movement amount. The movement amount is specified based on the receiving light image obtained using the image sensor 35, for example. The main control unit 211 repeatedly performs this processing. This allows to arrange the optical system so that the optical axis of the optical system substantially coincides with the axis of the subject's eye E and the distance of the optical system with respect to the subject's eye E is a predetermined working distance.

(S3: Perform OCT Scan)

Subsequently, the main control unit 211 controls the OCT unit 100 to perform OCT scan under the scan condition set in step S1.

Specifically, the main control unit 211 controls the optical scanner 42 to deflect the measurement light LS generated based on the light L0 emitted from the light source unit 101 and to scan a predetermined site (for example, fundus) of the subject's eye E with the deflected measurement light LS. The detection result of the interference light obtained by scanning with the measurement light LS is sampled in synchronization with the clock KC. The three-dimensional complex OCT data of the subject's eye E is acquired from the detection result of the interference light.

(S4: Perform Aberration Correction)

Next, the main control unit 211 controls the data processing unit 230 to perform aberration correction processing on the complex OCT data obtained in step S3. In step S4, as described later, the CAO filter (parameter(s)) is searched, and the CAO filter obtained by the search is applied to the complex OCT data. The details of step S4 will be described later.

(S5: Display?)

Next, the main control unit 211 determines whether or not to display the aberration information corresponding to the CAO filter searched in step S4 on the display unit 240A. For example, the main control unit 211 determines whether or not to display the aberration information on the display unit 240A based on the content operation of the user with respect to the operation unit 240B. For example, the main control unit 211 determines whether or not to display the aberration information on the display unit 240A depending on the operation mode designated in advance.

When it is determined that the aberration information is to be displayed on the display unit 240A in step S5 (step S5: Y), the operation of the ophthalmologic apparatus 1500b proceeds to step S6. When it is determined that the aberration information is not to be displayed on the display unit 240A in step S5 (step S5: N), the operation of the ophthalmologic apparatus 1500b proceeds to step S7.

(S6: Display Aberration Information)

When it is determined that the aberration information is to be displayed on the display unit 240A in step S5 (step S5: Y), the main control unit 211 displays the aberration information on the pupil surface of the subject's eye E corresponding to the parameter(s) of the CAO filter searched in step S4, on the display unit 240A. The aberration information includes a distribution map (phase distribution map) of the phase shift of the light on the pupil surface of the subject's eye E. At this time, the main control unit 211 may display the Zernike coefficients and/or the tomographic image and the projection image formed based on the complex OCT data to which the searched CAO filter is applied on the same screen as the distribution map.

(S7: Form OCT Image)

Following step S6, or when it is determined that the aberration information is not to be displayed on the display unit 240A in step S5 (step S5: N), the main control unit 211 controls the image forming unit 220 or the data processing unit 230 to form the OCT image formed based on the complex OCT data to which the CAO filter searched in step S4 is applied. Examples of the OCT image include the tomographic image, the projection image, the en-face image, the OCTA image, and the like.

In some embodiments, the process of step S7 is started based on the operation content of the operation unit 240B by the user.

This terminates the operation of the ophthalmologic apparatus 1500b (END).

The process of step S4 in FIG. 15 is performed as shown in FIG. 16.

(S11: Perform Phase Stabilization)

When the complex OCT data of the subject's eye E is acquired in step S4, the main control unit 211 controls the phase stabilization unit 231 to perform phase stabilization processing on the acquired complex OCT data.

The phase stabilization unit 231 performs phase stabilization processing on the three-dimensional complex OCT data of the subject's eye E, as described above. The details of step S11 will be described later.

(S12: Perform Fourier Transform)

Subsequently, the main control unit 211 performs known Fourier transform processing on the three-dimensional complex OCT data on which the phase stabilization processing has been performed in step S11 to convert into the OCT data in the frequency domain.

(S13: Perform Aberration Evaluation)

Next, the main control unit 211 controls the data processing unit 230 (filter information search unit 300) to perform aberration evaluation for searching for the CAO filter.

The filter information search unit 300 specifies the parameter(s) of the optimal CAO filter, by evaluating the image quality of the OCT image formed based on the complex OCT data to which the CAO filter has been applied while updating the parameter(s) of the CAO filter. The details of step S13 will be described later.

(S14: Perform Aberration Correction)

Next, the main control unit 211 corrects the aberration in the three-dimensional complex OCT data, by applying the CAO filter searched n step S13 to the three-dimensional complex OCT data of the subject's eye E acquired in step S3 in FIG. 15.

(S15: Perform Inverse Fourier Transform)

Subsequently, the main control unit 211 performs known inverse Fourier transform processing on the three-dimensional complex OCT data whose aberration has been corrected in step S14 to convert into the OCT data in the space domain.

This terminates the processing of step S4 in FIG. 15 (END).

Step S11 in FIG. 16 is performed as shown in FIG. 17.

(S11-1: Set Reference Data)

First, the phase stabilization unit 231 sets the data of a predetermined B-frame formed based on the three-dimensional complex OCT data as the reference data. For example, the data $B_1$ of the B-frame at the upper end in the three-dimensional complex OCT data is extracted as the reference data (see FIG. 12A).

(S11-2: Set Target Data)

Next, the phase stabilization unit 231 sets the data $B_2$ of the B-frame adjacent in the y direction to the reference data $B_1$ extracted from the data of the predetermined B-frame formed based on the three-dimensional complex OCT data as the target data.

(S11-3: Generate Phase Difference Profile)

Subsequently, the phase difference profile generator 231A calculates the phase difference for each depth position of the A-lines between the data $B_1$ and $B_2$ of two adjacent B-frames. The phase difference profile generator 231A generates the phase difference profile in which the phase differences for each A-line, which are obtained by performing averaging processing in the z direction on the calculated phase differences are arranged in the B-line direction.

(S11-4: Remove Phase Difference Data)

Subsequently, the phase difference data removal unit 231C removes the less reliable phase difference data from the phase difference profile generated in step S11-3.

For example, the phase difference data removal unit 231C removes the phase difference data that satisfies Equation (2) or (3) from the phase difference profile generated in step S11-3.

(S11-5: Extract Phase Drift)

Subsequently, the phase drift extraction unit 231B performs at least one of the smoothing processing, the polynomial fitting, and the high frequency cut filtering processing on the phase difference profile from which the less reliable phase difference data is removed in step S11-4, and extracts the phase drift.

(S11-6: Perform Phase Correction)

Subsequently, the phase correction unit 231D corrects the phase of the target data based on the phase drift extracted in step S11-5, as described above.

(S11-7: End?)

Next, the phase stabilization unit 231 (or main control unit 211) determines whether or not to be ended the phase stabilization processing. For example, the phase stabilization unit 231 determines whether or not to be ended by determining whether or not the phase stabilization processing has been performed on all B-frame data in the three-dimensional complex OCT data.

When it is determined that the phase stabilization processing is to be ended in step S11-7 (step S11-7: Y), the operation of step S11 is terminated (END). When it is determined that the phase stabilization processing is not to be ended in step S11-7 (step S11-7: N), the operation of step S11 proceeds to step S11-8.

(S11-8: Set Target Data to Reference Data)

When it is determined that the phase stabilization processing is not to be ended in step S11-7 (step S11-7: N), the phase stabilization unit 231 sets the target data to the reference data. After that, the operation of the phase stabilization unit 231 proceeds to, step S11-2.

For example, the phase stabilization unit 231 sets the data $B_2$ of the B-frame to the reference data. Thereby, in the next step S11-2, the data $B_3$ of the B-frame adjacent in the y direction to the data $B_2$ of the B-frame is set as the target data, and phase correction is performed between the data $B_2$ and $B_3$ of the B-frames. The phase correction process described above is performed sequentially for data of all B-frames in the three-dimensional complex OCT data.

FIG. 18 shows a diagram for explaining the operation of steps S12 to S15 in FIG. 16.

In step S12, the complex OCT data OD1 on which the phase stabilization processing has been performed in step S11 is converted into the OCT data FD1 in the frequency domain. In steps S13 and S14, the CAO filter CF searched in the frequency domain is applied to the complex OCT data FD1, and the aberration in the complex OCT data is corrected. In step S15, the complex OCT data in which the aberration has been corrected is converted into the OCT data OD2 in the space domain.

The process of step S13 in FIG. 16 is performed as shown in FIG. 19.

(S21: Generate Filter Information)

The main control unit 211 controls the filter information generator 232 to generate the parameter(s) of the CAO filter.

The filter information generator 232 acquires the predetermined initial value and generates it as the parameter(s) of the CAO filter. In case that the refractive power information of the subject's eye E is acquired from the external ophthalmologic apparatus, the filter information generator 232 generates the parameter(s) of the CAO filter from the refractive power information. In case that the past CAO filter is reused, the filter information generator 232 generates the parameter(s) of the CAO filter by reading out the parameter(s) of the past CAO filter stored in the storage unit 212.

Subsequently, the main control unit 211 controls the rough search unit 310 to perform rough search processing of steps S22 to S24, and then controls the fine search unit 320 to perform fine search processing of step S25.

(S22: Search for Coefficient of Defocus Term)

First, the main control unit 211 controls the rough search unit 310 to search for the coefficient $C_{de}$ of the defocus term of the CAO filter in FIG. 8. The details of step S22 will be described later.

(S23: Search for Coefficient of Astigmatism Term in HV Direction)

Subsequently, the main control unit 211 controls the rough search unit 310 to search for the coefficient $C_{as\_HV}$ of the astigmatism term in the HV direction of the CAO filter in FIG. 8. The process of step S23 is performed in the same manner as in step S22.

(S24: Search for Coefficient of Astigmatism Term in Diagonal Direction)

Subsequently, the main control unit 211 controls the rough search unit 310 to search for the coefficient $C_{as\_DG}$ of the astigmatism term in the diagonal direction of the CAO filter in FIG. 8. The process of step S24 is performed in the same manner as in step S22.

(S25: Perform Fine Search)

Next, the main control unit 211 controls the fine search unit 320 to perform fine search processing of the coefficients described above of the CAO filter in FIG. 8. The details of step S25 will be described later.

This terminates the processing of step S13 in FIG. 16 (END).

Each of steps S22 to S24 in FIG. 19 is performed as shown in FIG. 20. That is, the search process of the coefficient $C_{de}$ of the defocus term in step S22 is performed as shown in FIG. 20, and the search process of the coefficient $C_{as\_HV}$ of the astigmatism term in the HV direction in step S23 is performed as shown in FIG. 20. Further, the search process of the coefficient $C_{as\_DG}$ of the astigmatism term in the diagonal direction in step S24 is performed as shown in FIG. 20.

(S31: Perform Filter Test)

The rough search unit 310 applies the CAO filter whose coefficient is set at the present stage to the complex OCT data in the filter test unit 311, and performs filter test for evaluating the image quality of the OCT image formed based on the complex OCT data to which the CAO filter has been applied. In the filter test, the image quality evaluation value of the formed OCT image is calculated. The details of step S31 will be described later.

(S32: End?)

Subsequently, the rough search unit 310 (or the main control unit 211) determines whether or not to end the filter test performed while sequentially updating the coefficient. For example, the rough search unit 310 determines that the filter test is to be continued when the updating coefficient are within a predetermined search range, and determines that the filter test is to be ended when the updating coefficient exceeds the search range. For example, the rough search unit 310 determines that the filter test is to be continued when the number of updates of the predetermined coefficient is less than or equal to a threshold, and determines that the filter test is to be ended when the number of the update exceeds the threshold.

When it is determined that the filter test is to be ended in step S32 (step S32: Y), the operation of the rough search unit 310 proceeds to step S34. When it is determined that the filter test is not to be ended in step S32 (step S32: N), the operation of the rough search unit 310 proceeds to step S33.

(S33: Update Coefficient)

When it is determined that the filter is not to be ended in step S32 (step S32: N), the filter information update unit 312 increases the coefficient by a predetermined increase or decreases it by a predetermined decrease. After that, the operation of the rough search unit 310 proceeds to step S31.

(S34: Specify Coefficient)

When it is determined that the filter test is to be ended in step S32 (step S32: Y), the rough search unit 310 specifies the coefficient of the CAO filter.

The rough search unit 310 specifies the coefficient of the CAO filter applied to the OCT image having the best image quality based on a plurality of image quality evaluation values obtained by repeatedly performing the filter test in step S31. For example, the rough search unit 310 specifies the coefficient of the CAO filter applied to the OCT image having the maximum image quality evaluation value or the minimum image quality evaluation value.

This terminates each of the processing of steps S22 to S24 in FIG. 19 (END).

The process of step S31 in FIG. 20 is performed as shown in FIG. 21.

(S41: Perform Filter Processing)

The filter test unit 311 applies the CAO filter to the complex OCT data, in the filter processing unit 311A.

(S42: Perform Inverse Fourier Transform)

Subsequently, the filter test unit 311 (data processing unit 230) performs inverse Fourier transform on the complex OCT data on which the filter processing has been performed in step S41, and generates the complex OCT data in the space domain.

(S43: Form Projection Image)

Next, the projection image forming unit 235 forms the projection image based on the complex OCT data in the space domain formed in step S43.

(S44: Calculate Image Quality Evaluation Value)

Subsequently, the image quality evaluation unit 311B calculates the image quality evaluation value of the projection image formed in step S43.

This terminates the processing of step S31 in FIG. 20 (END).

The process of step S25 in FIG. 19 is performed as shown in FIG. 22.

(S51: Perform Filter Test)

The fine search unit 320 applies the CAO filter to the complex OCT data, in the filter test unit 321. After that, the filter test unit 321 performs filter test for evaluating the image quality of the OCT image formed based on the complex OCT data to which the CAO filter has been applied. The process in step S51 is performed in the same manner as the process in step S31 (steps S41 to S44) (see FIG. 21). That is, the image quality evaluation value is calculated also in step S51.

(S52: Save Image Quality Evaluation Value)

Subsequently, the fine search unit 320 stores the image quality evaluation value calculated in step S51 in a storage unit such as the storage unit 212.

(S53: End?)

Next the fine search unit 320 (or the main control unit 211) determines whether or not to end the filter test performed while sequentially updating the coefficient. For example, when the degree of improvement in image quality is equal to or less than a predetermined threshold value based on the image quality evaluation value stored in step S52, the fine search unit 320 judges that it is difficult to further improve the image quality, and determines that the filter test is to be ended. When the degree of improvement in image quality exceeds the threshold, the fine search unit 320 judges that it is possible to further improve the image quality, and determines that the filter test is to be continued. The degree of improvement in image quality corresponds to a gradient of the image quality evaluation value. Alternatively, for example, the fine search unit 320 determines that the filter test is to be continued when the number of updates of the predetermined coefficient is less than or equal to a threshold, and determines that the filter test is to be ended when the number of the update exceeds the threshold.

When it is determined that the filter test is to be ended in step S53 (step S53: Y), the operation of the fine search unit 320 proceeds to step S56. When it is determined that the filter test is not to be ended in step S53 (step S53: N), the operation of the fine search unit 320 proceeds to step S54.

(S54: Analyze Gradient)

When it is determined that the filter test is not to be ended in step S53 (step S53: N), the fine search unit 320 calculates the gradient when each coefficient of the CAO filter is slightly changed in the gradient calculator 323. The details of step S54 will be described later.

(S55: Update Coefficient)

Subsequently, the filter information update unit 322 updates the coefficient of the CAO filter by the amount of change according to the gradient calculated in step S54. After that, the operation of the fine search unit 320 proceeds to step S51.

(S56: Specify Coefficient)

When it is determined that the filter test is to be ended in step S53 (step S53: Y), the fine search unit 320 specifies the coefficient of the CAO filter.

For example, in step S53, in case that it is determined that the filter test is to be ended when the degree of improvement in image quality is equal to or less than the predetermined threshold value, the fine search unit 320 specifies the coefficient of the CAO filer applied to the OCT image having the image quality evaluation value stored in step S52.

For example, in step S53, in case that it is determined that the filter test is to be ended when the number of the update of the predetermined coefficient exceeds the threshold, the fine search unit 320 specifies the coefficient of the CAO filter applied to the OCT image having the best image quality, based on the plurality of image quality evaluation values obtained by repeatedly performing the filter test in step S51. For example, the fine search unit 320 specifies the coefficient of the CAO filter applied to the OCT image having the maximum image quality evaluation value or the minimum image quality evaluation value.

This terminates the processing of step S25 in FIG. 19 (END).

The process of step S54 in FIG. 22 is performed as shown in FIG. 23. FIG. 23 shows a processing example for searching for the defocus term, the astigmatism term in the HV direction, the astigmatism term in the diagonal direction, and a spherical aberration term of the CAO filter. It should be noted that FIG. 23 shows a processing example in which a plurality of coefficients of the CAO filter shown in FIG. 8 is sequentially searched. However, the processing is executed so as to search for a plurality of coefficients of the CAO filter shown in FIG. 8 in parallel.

(S61: $C_{De}$?)

The fine search unit 320 determines whether or not the coefficient to be searched is the coefficient $C_{de}$ of the defocus term.

When it is determined that the coefficient to be searched is the coefficient $C_{de}$ of the defocus term (step S61: Y), the fine search unit 320 performs the processing in steps S61-1 to S61-5. When it is determined that the coefficient to be searched is not the coefficient $C_{de}$ of the defocus term (step S61: N), the operation of the fine search unit 320 proceeds to step S62.

(S61-1: Update Coefficient to ($C_{de}+\delta$))

When it is determined that the coefficient to be searched is the coefficient $C_{de}$ of the defocus term in step S61 (step S61: Y), the filter information update unit 322 updates the coefficient $C_{de}$ to "$C_{de}+\delta$".

(S61-2: Perform Filter Test)

Subsequently, the filter test unit 321 applies the CAO filter whose coefficient is updated in step S61-1 to the complex OCT data, and performs filter test for evaluating the image quality of the OCT data formed based on the complex OCT data to which the CAO filter has been applied. The process in step S61-1 is performed in the same manner as the process in step S31 (steps S41 to S44) (see FIG. 21). The image quality evaluation value is calculated in step S61-2.

(S61-3: Update Coefficient to ($C_{de}-\delta$))

The filter information update unit 322 updates the coefficient $C_{de}$ to "$C_{de}-\delta$".

(S61-4: Perform Filter Test)

Subsequently, the filter test unit 321 applies the CAO filter whose coefficient is updated in step S61-3 to the complex OCT data, and performs filter test for evaluating the image quality of the OCT data formed based on the complex OCT data to which the CAO filter has been applied. The process in step S61-3 is performed in the same manner as the process in step S31 (steps S41 to S44) (see FIG. 21). The image quality evaluation value is calculated in step S61-3.

(S61-5: Calculate Gradient)

Subsequently, the gradient calculator 323 calculates the gradient of the image quality evaluation value based on the image quality evaluation value calculated in step S61-2 and the image quality evaluation value calculated in step S61-4. After that, the operation of the fine search unit 320 proceeds to step S61.

(S62: $C_{as\_HV}$?)

When it is determined that the coefficient to be searched is not the coefficient $C_{de}$ of the defocus term in step S61 (step S61: N), the fine search unit 320 determines whether or not the coefficient to be searched is the coefficient $C_{as\_HV}$ of the astigmatism term in the HV direction.

When it is determined that the coefficient to be searched is the coefficient $C_{as\_HV}$ of the astigmatism term in the HV direction in step S62 (step S62: Y), the fine search unit 320 performs the processing in steps S62-1 to S62-5. When it is determined that the coefficient to be searched is not the coefficient $C_{as\_HV}$ of the astigmatism term in the HV direction (step S62: N), the operation of the fine search unit 320 proceeds to step S63.

(S62-1: Update Coefficient to ($C_{as\_HV}+\delta$))

When it is determined that the coefficient to be searched is the coefficient $C_{as\_HV}$ of the astigmatism term in the HV direction in step S62 (step S62: Y), the filter information update unit 322 updates the coefficient $C_{as\_HV}$ to "$C_{as\_HV}+\delta$" in the same manner as in step S61-1. "$\delta$" in step S62-1 may be different from "$\delta$" in step S61-1.

(S62-2: Perform Filter Test)

Subsequently, in the same manner as in step S61-1, the filter test unit 321 applies the CAO filter whose coefficient is updated in step S62-1 to the complex OCT data, and performs filter test for evaluating the image quality of the OCT data formed based on the complex OCT data to which the CAO filter has been applied (see FIG. 21).

(S62-3: Update Coefficient to ($C_{as\_HV}-\delta$))

Subsequently, the filter information update unit 322 updates the coefficient $C_{as\_HV}$ to "$C_{as\_HV}-\delta$", in the same manner as in step S61-3.

(S62-4: Perform Filter Test)

Subsequently, in the same manner as in step S61-4, the filter test unit 321 applies the CAO filter whose coefficient is updated in step S62-3 to the complex OCT data, and performs filter test for evaluating the image quality of the OCT data formed based on the complex OCT data to which the CAO filter has been applied (see FIG. 21).

(S62-5: Calculate Gradient)

Subsequently, in the same manner as in step S61-5, the gradient calculator 323 calculates the gradient of the image quality evaluation value based on the image quality evaluation value calculated in step S62-2 and the image quality evaluation value calculated in step S62-4. After that, the operation of the fine search unit 320 proceeds to step S61.

(S63: $C_{as\_DG}$?)

When it is determined that the coefficient to be searched is not the coefficient $C_{as\_HV}$ of the defocus term in step S62 (step S62: N), the fine search unit 320 determines whether or not the coefficient to be searched is the coefficient $C_{as\_DG}$ of the astigmatism term in the diagonal direction.

When it is determined that the coefficient to be searched is the coefficient $C_{as\_DG}$ of the astigmatism term in the diagonal direction in step S63 (step S63: Y), the fine search unit 320 performs the processing in steps S63-1 to S63-5. When it is determined that the coefficient to be searched is not the coefficient $C_{as\_DG}$ of the astigmatism term in the diagonal direction (step S63: N), the operation of the fine search unit 320 proceeds to step S64.
(S63-1: Update Coefficient to $(C_{as\_DG}+\delta)$)
(S63-2: Perform Filter Test)
(S63-3: Update Coefficient to $(C_{as\_DG}-\delta)$)
(S63-4: Perform Filter Test)
(S63-5: Calculate Gradient)
When it is determined that the coefficient to be searched is the coefficient $C_{as\_DG}$ of the astigmatism term in the diagonal direction in step S63 (step S63: Y), the fine search unit 320 calculates the gradient of the image quality evaluation value for the coefficient $C_{as\_DG}$ of the astigmatism term in the diagonal direction, in the same manner as in steps S61-1 to S61-5 (steps S63-1 to S63-5). After that, the operation of the fine search unit 320 proceeds to step S61. The processes of steps S63-1 to S63-5 are the same as the processes of steps S61-1 to S61-5. Thereby, detailed description thereof will be omitted.
(S64: $C_{sph}$?)
When it is determined that the coefficient to be searched is not the coefficient $C_{as\_DG}$ of the defocus term in the diagonal direction in step S63 (step S63: N), the fine search unit 320 determines whether or not the coefficient to be searched is the coefficient $C_{sph}$ of the spherical aberration term.
When it is determined that the coefficient to be searched is the coefficient $C_{sph}$ of the spherical aberration term in step S64 (step S64: Y), the fine search unit 320 performs the processing in steps S64-1 to S64-5.
(S64-1: Update Coefficient to $(C_{sph}+\delta)$)
(S64-2: Perform Filter Test)
(S64-3: Update Coefficient to $(C_{sph}-\delta)$)
(S64-4: Perform Filter Test)
(S64-5: Calculate Gradient)
When it is determined that the coefficient to be searched is the coefficient $C_{sph}$ of the spherical aberration term in step S64 (step S64: Y), the fine search unit 320 calculates the gradient of the image quality evaluation value for the coefficient $C_{sph}$ of the spherical aberration term, in the same manner as in steps S61-1 to S61-5 (steps S64-1 to S64-5). After that, the operation of the fine search unit 320 proceeds to step S61. The processes of steps S64-1 to S64-5 are the same as the processes of steps S61-1 to S61-5. Thereby, detailed description thereof will be omitted.
When it is determined that the coefficient to be searched is not the coefficient $C_{sph}$ of the spherical aberration term in step S64 (step S64: N), the operation of the fine search unit 320 executes the same processing for the coefficients in the next term. It should be noted that the process of step S54 in FIG. 22 is terminated when the coefficients of all the terms are terminated.

Modification Examples

In the above embodiments, the parameter(s) (filter information) of the CAO filter according to the embodiments may be configured to be searched for each OCT measurement region (for each angle of view) in the subject's eye E. In this case, the aberration information on the pupil surface of the subject's eye E corresponding to the parameter(s) of the CAO filter searched for each OCT measurement region in the subject's eye E may be displayed on the display unit 240A.

In some embodiments, a program for causing a computer to execute the ophthalmologic information processing method described above is provided. Such a program can be stored in any non-transitory recording medium that can be read by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

[Actions]

Hereinafter, the ophthalmologic information processing apparatus, the ophthalmologic apparatus, the ophthalmologic information processing method, and the program according to the embodiments will be described.

An ophthalmologic information processing apparatus (ophthalmologic information processing apparatus 1200, ophthalmologic information processing unit 1200a, 1200b, data processing unit 230) includes a generator (phase difference profile generator 231A), an extractor (phase drift extraction unit 231B), and a phase correction unit (231D). The generator is configured to generate a phase difference profile by performing averaging processing in a depth direction on phase differences obtained by calculating for each depth position of A-lines between two adjacent B-frames of complex OCT data of a subject's eye (E). The extractor is configured to a phase drift from the phase difference profile generated by the generator. The phase correction unit is configured to correct a phase of first complex OCT data of either one of the two B-frames based on the phase drift extracted by the extractor.

According to such an aspect, OCT data that is not affected by phase changes caused by the movement of the subject's eye or phase instability in the OCT measurement system can be acquired with simple processing. Thereby, the accuracy of the phase information obtained from the OCT data can be improved.

Some embodiments further include a removal unit (phase difference data removal unit 231C) configured to remove less reliable phase difference data from the phase difference profile. The extractor is configured to extract the phase drift, from which a local phase difference change has been removed, from the phase difference profile from which the less reliable phase difference data has been removed by the removal unit.

According to such an aspect, OCT data robust to local phase noise can be acquired.

In some embodiments, the less reliable phase difference data includes at least one of data whose signal strength is less than a predetermined threshold level and data in which a contribution of the phase difference at a predetermined depth position exceeds a predetermined threshold in the averaging processing.

According to such an aspect, OCT data robust to local phase noise can be acquired with simple processing.

In some embodiments, the extractor is configured to extract the phase drift by performing at least one of smoothing processing, polynomial fitting, and high frequency cut filtering processing on the phase difference profile.

According to such an aspect, OCT data that is not affected by phase changes caused by the movement of the subject's eye or phase instability in the OCT measurement system can be acquired with even simpler processing.

In some embodiments, a parameter of at least one of the smoothing processing, the polynomial fitting, and the high frequency cut filtering processing is set based on at least one of a frequency of phase change in a measurement system for acquiring the complex OCT data, a speed of the phase change, and time required for an OCT scan in the measurement system.

According to such an aspect, the phase drift can be extracted under the optimal conditions corresponding to the acquisition environment of complex OCT data.

In some embodiments, for a first B-frame and a second B-frame adjacent to each other, after correcting the phase of the complex OCT data of the second B-frame based on the phase difference profile generated by the generator, for the second B-frame and a third B-frame adjacent to the second B-frame, the phase of the complex OCT data of the third B-frame is corrected based on the phase difference profile generated by the generator.

According to such an aspect, the phase of the three-dimensional complex OCT data can be stabilized with simple processing.

Some embodiments further include an image forming unit (image forming unit 220, data processing unit 230) configured to form an OCT image of the subject's eye based on the complex OCT data of the subject's eye, in which the complex OCT data of at least one B-frame is corrected by the phase correction unit.

According to such an aspect, OCT images robust to phase changes caused by the movement of the subject's eye or phase instability in the OCT measurement system can be formed.

An ophthalmologic apparatus (1500a, 1500b) includes a measurement system (OCT optical system 1101, OCT optical system 8) configured to acquire the complex OCT data by performing optical coherence tomography on the subject's eye; and the ophthalmologic information processing apparatus of any one of described above.

According to such an aspect, the ophthalmologic apparatus capable of acquiring OCT data that is not affected by phase changes caused by the movement of the subject's eye or phase instability in the OCT measurement system with simple processing can be provided.

An ophthalmologic information processing method according to the embodiments includes a generation step, an extraction step, and a phase correction step. The generation step is performed to generate a phase difference profile by performing averaging processing in a depth direction on phase differences obtained by calculating for each depth position of A-lines between two adjacent B-frames of complex OCT data of a subject's eye (E). The extraction step is performed to extract a phase drift from the phase difference profile generated in the generation step. The phase correction step is performed to correct a phase of first complex OCT data of either one of the two B-frames based on the phase drift extracted in the extraction step.

According to such an aspect, OCT data that is not affected by phase changes caused by the movement of the subject's eye or phase instability in the OCT measurement system can be acquired with simple processing. Thereby, the accuracy of the phase information obtained from the OCT data can be improved.

Some embodiments further include a removal step of removing less reliable phase difference data from the phase difference profile. The extraction step is performed to extract the phase drift, from which a local phase difference change has been removed, from the phase difference profile from which the less reliable phase difference data has been removed in the removal step.

According to such an aspect, OCT data robust to local phase noise can be acquired.

In some embodiments, the less reliable phase difference data includes at least one of data whose signal strength is less than a predetermined threshold level and data in which a contribution of the phase difference at a predetermined depth position exceeds a predetermined threshold in the averaging processing.

According to such an aspect, OCT data robust to local phase noise can be acquired with simple processing.

In some embodiments, the extraction step is performed to extract the phase drift by performing at least one of smoothing processing, polynomial fitting, and high frequency cut filtering processing on the phase difference profile.

According to such an aspect, OCT data that is not affected by phase changes caused by the movement of the subject's eye or phase instability in the OCT measurement system can be acquired with even simpler processing.

In some embodiments, a parameter of at least one of the smoothing processing, the polynomial fitting, and the high frequency cut filtering processing is set based on at least one of a frequency of phase change in a measurement system for acquiring the complex OCT data, a speed of the phase change, and time required for an OCT scan in the measurement system.

According to such an aspect, the phase drift can be extracted under the optimal conditions corresponding to the acquisition environment of complex OCT data.

In some embodiments, for adjacent first B-frame and second B-frame, after correcting the phase of the complex OCT data of the second B-frame based on the phase difference profile generated in the generation step, for the second B-frame and a third B-frame adjacent to the second B-frame, the phase of the complex OCT data of the third B-frame is corrected based on the phase difference profile generated in the generation step.

According to such an aspect, the phase of the three-dimensional complex OCT data can be stabilized with simple processing.

Some embodiments further include an image forming step of forming an OCT image of the subject's eye based on the complex OCT data of the subject's eye, in which the complex OCT data of at least one B-frame is corrected in the phase correction step.

According to such an aspect, OCT images robust to phase changes caused by the movement of the subject's eye or phase instability in the OCT measurement system can be formed.

A program according to the embodiments causes a computer to execute each step of the ophthalmologic information processing method of any one of described above.

According to such an aspect, OCT data that is not affected by phase changes caused by the movement of the subject's eye or phase instability in the OCT measurement system can be acquired with simple processing. Thereby, the accuracy of the phase information obtained from the OCT data can be improved.

<Others>

In the above embodiments, the case where the swept source type OCT is used has been described. However, the spectral domain type OCT may be used. In this case, a low coherence light source (for example, an SLD light source etc.) is used instead of the wavelength sweeping light source, in the light source unit 101. And a spectrometer and an image sensor (for example, a CCD etc.) are used instead of the detector 125, in the interference optical system.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic information processing apparatus, comprising:
   a generator circuit configured to generate a phase difference profile by performing averaging processing in a depth direction on phase differences obtained by calculating for each depth position of A-lines between two adjacent B-frames of complex OCT data of a subject's eye;
   an extractor circuit configured to extract a phase drift from the phase difference profile generated by the generator circuit; and
   a phase correction circuit configured to correct a phase of first complex OCT data of either one of the two B-frames based on the phase drift extracted by the extractor circuit.

2. The ophthalmologic information processing apparatus of claim 1, further comprising
   a removal circuit configured to remove less reliable phase difference data from the phase difference profile, wherein
   the extractor circuit is configured to extract the phase drift, from which a local phase difference change has been removed, from the phase difference profile from which the less reliable phase difference data has been removed by the removal circuit.

3. The ophthalmologic information processing apparatus of claim 2, wherein
   the less reliable phase difference data includes at least one of data whose signal strength is less than a predetermined threshold level and data in which a contribution of the phase difference at a predetermined depth position exceeds a predetermined threshold in the averaging processing.

4. The ophthalmologic information processing apparatus of claim 1, wherein
   the extractor circuit is configured to extract the phase drift by performing at least one of smoothing processing, polynomial fitting, and high frequency cut filtering processing on the phase difference profile.

5. The ophthalmologic information processing apparatus of claim 4, wherein
   a parameter of at least one of the smoothing processing, the polynomial fitting, and the high frequency cut filtering processing is set based on at least one of a frequency of phase change in a measurement system for acquiring the complex OCT data, a speed of the phase change, and time required for an OCT scan in the measurement system.

6. The ophthalmologic information processing apparatus of claim 1, wherein
   for a first B-frame and a second B-frame adjacent to each other, after correcting the phase of the complex OCT data of the second B-frame based on the phase difference profile generated by the generator circuit,
   for the second B-frame and a third B-frame adjacent to the second B-frame, the phase of the complex OCT data of the third B-frame is corrected based on the phase difference profile generated by the generator circuit.

7. The ophthalmologic information processing apparatus of claim 1, further comprising
   an image forming circuit configured to form an OCT image of the subject's eye based on the complex OCT data of the subject's eye, in which the complex OCT data of at least one B-frame is corrected by the phase correction circuit.

8. An ophthalmologic apparatus, comprising:
   a measurement system configured to acquire the complex OCT data by performing optical coherence tomography on the subject's eye; and
   the ophthalmologic information processing apparatus of claim 1.

9. An ophthalmologic information processing method, comprising:
   a generation step of generating a phase difference profile by performing averaging processing in a depth direction on phase differences obtained by calculating for each depth position of A-lines between two adjacent B-frames of complex OCT data of a subject's eye;
   an extraction step of extracting a phase drift from the phase difference profile generated in the generation step; and
   a phase correction step of correcting a phase of first complex OCT data of either one of the two B-frames based on the phase drift extracted in the extraction step.

10. The ophthalmologic information processing method of claim 9, further comprising
    a removal step of removing less reliable phase difference data from the phase difference profile, wherein
    the extraction step is performed to extract the phase drift, from which a local phase difference change has been removed, from the phase difference profile from which the less reliable phase difference data has been removed in the removal step.

11. The ophthalmologic information processing method of claim 10, wherein
    the less reliable phase difference data includes at least one of data whose signal strength is less than a predetermined threshold level and data in which a contribution of the phase difference at a predetermined depth position exceeds a predetermined threshold in the averaging processing.

12. The ophthalmologic information processing method of claim 9, wherein
    the extraction step is performed to extract the phase drift by performing at least one of smoothing processing, polynomial fitting, and high frequency cut filtering processing on the phase difference profile.

13. The ophthalmologic information processing method of claim 12, wherein
    a parameter of at least one of the smoothing processing, the polynomial fitting, and the high frequency cut filtering processing is set based on at least one of a frequency of phase change in a measurement system for acquiring the complex OCT data, a speed of the phase change, and time required for an OCT scan in the measurement system.

14. The ophthalmologic information processing method of claim 9, wherein
    for adjacent first B-frame and second B-frame, after correcting the phase of the complex OCT data of the second B-frame based on the phase difference profile generated in the generation step,
    for the second B-frame and a third B-frame adjacent to the second B-frame, the phase of the complex OCT data of the third B-frame is corrected based on the phase difference profile generated in the generation step.

15. The ophthalmologic information processing method of claim 9, further comprising
an image forming step of forming an OCT image of the subject's eye based on the complex OCT data of the subject's eye, in which the complex OCT data of at least one B-frame is corrected in the phase correction step.

16. A computer readable non-transitory recording medium in which a program for causing a computer to execute each step of the ophthalmologic information processing method of claim 9 is recorded.

* * * * *